United States Patent
Barvian et al.

(10) Patent No.: US 6,906,094 B2
(45) Date of Patent: Jun. 14, 2005

(54) 1,2,4-TRIBSUBSTITUTED BENZENES AS INHIBITORS OF 15-LIPOXYGENASE

(75) Inventors: Nicole Chantel Barvian, Ann Arbor, MI (US); Patrick Michael O'Brien, Stockbridge, MI (US); William Chester Patt, Chelsea, MI (US); Joseph Armand Picard, Canton, MI (US); Drago Robert Sliskovic, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 135 days.

(21) Appl. No.: 10/362,104

(22) PCT Filed: May 8, 2001

(86) PCT No.: PCT/US01/14795

§ 371 (c)(1), (2), (4) Date: Feb. 21, 2003

(87) PCT Pub. No.: WO01/96298

PCT Pub. Date: Dec. 20, 2001

(65) Prior Publication Data

US 2004/0053983 A1 Mar. 18, 2004

Related U.S. Application Data

(60) Provisional application No. 60/211,498, filed on Jun. 14, 2000.

(51) Int. Cl.$^7$ .................... A61K 31/404; C07D 209/04

(52) U.S. Cl. ...................................... 514/415; 548/490

(58) Field of Search ................ 548/490; 514/415

(56) References Cited

U.S. PATENT DOCUMENTS

| | | | |
|---|---|---|---|
| 4,595,780 A | 6/1986 | Ogata et al. | 564/79 |
| 6,268,387 B1 | 7/2001 | Connor et al. | 514/352 |
| 2001/0031874 A1 | 10/2001 | Connor et al. | |

FOREIGN PATENT DOCUMENTS

| | | |
|---|---|---|
| DE | 4238233 | 5/1994 |
| EP | 0148725 | 7/1985 |
| WO | 9932433 | 7/1999 |
| WO | 0196299 | 12/2001 |

*Primary Examiner*—Golam M M Shameem
(74) *Attorney, Agent, or Firm*—Charles W. Ashbrook; Eric J. Baude; Claude F. Purchase, Jr.

(57) ABSTRACT

The present invention provides compounds of formula (I) wherein R, Z, Y, W, $R_5$, V, and X are as defined in the description, and pharmaceutically acceptable salts thereof, which are useful for the treatment of diseases responsive to the inhibition of the enzyme 15-lipoxygenase. Thus, the compounds of formula (I) and their pharmaceutically acceptable salts are useful for treating diseases with an inflammatory component, including atherosclerosis, diseases involving chemotaxis of monocytes, inflammation, stroke, coronary artery disease, asthma, arthritis, colorectal cancer, and psoriasis.

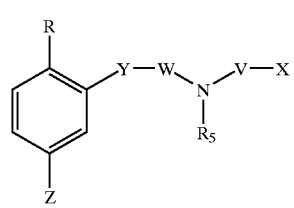

(I)

16 Claims, No Drawings

1,2,4-TRIBSUBSTITUTED BENZENES AS INHIBITORS OF 15-LIPOXYGENASE

This application claims the benefit of PCT/US01/14795 filed May 8, 2001, which claims the benefit of U.S. Provisional Application 60/211,498 filed Jun. 14, 2000; the entire contents of each of which are hereby incorporated herein by reference.

FIELD OF THE INVENTION

The present invention provides inhibitors of the enzyme 15-lipoxygenase, pharmaceutical compositions comprising said inhibitors, and methods of treating diseases responsive to inhibition of 15-lipoxygenase.

BACKGROUND OF THE INVENTION

Hypercholesterolemia can induce monocytes to migrate into the arterial wall and mature into foam cells or tissue macrophages that accumulate fatty material, including cholesterol esters. For example, continued creation of foam cells thickens the inner lining of medium and large arteries, thereby forming atherosclerotic plaques or lesions containing cholesterol, smooth muscle cells, and connective tissue cells. Affected arteries lose elasticity and become narrowed or obstructed by the plaques. These events are the hallmark of the disease atherosclerosis. Furthermore, atherosclerotic plaques may collect calcium, become brittle, and even rupture, triggering the formation of a blood clot or thrombus capable of occluding an artery and causing a stroke or a heart attack. In addition to atherosclerosis, hypercholesterolemia plays a role in peripheral vascular diseases of small arteries, veins, and lymphatics. Thus, hypercholesterolemia may also affect the arms, legs, kidneys, and other vital organs in addition to the heart and brain.

Cholesterol is transported in blood in particles called lipoproteins, which include low-density lipoproteins (LDL). Lipoproteins also contain cholesterol and are necessary for foam cell formation.

Lipoxygenases are enzymes that catalyze the oxidation of polyunsaturated fatty acids and esters thereof, including those found in low-density lipoproteins. For example, the enzyme 15-lipoxygenase (15-LO) oxidizes esterified polyenoic fatty acids. 15-LO has been implicated in inflammatory disorders and in the origin and recruitment of foam cells. In addition to modifying lipoproteins involved in the formation of foam cells, 15-LO also mediates an inflammatory reaction in the atherosclerotic lesion In human monocytes, 15-LO is induced by the cytokine IL-4.

Inhibitors of 15-LO are therefore useful to prevent and treat diseases with an inflammatory component such as asthma, psoriasis, osteoarthritis, rheumatoid arthritis, colorectal cancer, and atherosclerosis. For example, it has been shown that treatment with an inhibitor of 15-LO suppressed atherogenesis, or the production of atheroma, a fatty degeneration of the arterial wall, in rabbits fed a high-fat diet A chief object of this invention is to provide new 1,2,4-trisubstituted benzenes that are potent inhibitors of 15-LO.

SUMMARY OF THE INVENTION

The invention provides 1,2,4-trisubstituted benzenes, compositions of matter containing said benzenes, and methods for treating diseases related to the 15-LO cascade using such compounds or compositions. The invention provides compounds of Formula I:

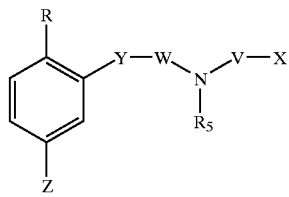

wherein:
R is OH, O—$C_1$–$C_4$ alkyl, or halo;
X is $R_1$, $OR_1$, $SR_1$, $NHR_1$, or $NR_1R_2$, wherein
$R_1$ and $R_2$ are independenty selected from $C_1$–$C_{12}$ alkyl $C_2$–$C_{12}$ alkenyl, $C_2$–$C_{12}$ alkynyl, benzyl, $C_3$–$C_7$ cycloalkyl, $C_2$–$C_6$ heteroaryl, $C_2$–$C_6$ heteroalkyl, and phenyl,
wherein the alkyl alkenyl, alkynyl, heterocyclic radical, benzyl, and phenyl groups are optionally substituted with from 1 to 5 substituents independently selected from halo, $NHR_3$, $CF_3$, $C_1$–$C_6$ alkyl, $OR_4$, $CO_2R_3$, $NO_2$, and $SR_3$,
wherein $R_3$ and $R_4$ are independently H or $C_1$–$C_6$ alkyl;
W and V are independently $SO_2$ or C=O, provided that when W is $SO_2$, —V— can further be a covalent bond and X can further be hydrogen;
$R_5$ is H, $C_1$–$C_6$ alkyl, or benzyl, wherein benzyl is optionally substituted with $R_1$, wherein $R_1$ is as defined above, or $R_5$ is a pharmaceutically acceptable cation;
Y is $NR_6$ or O, wherein $R_6$ is H or $C_1$–$C_6$ alkyl;
Z is 2-indolyl, 3-indolyl, 2-benzimidazolyl, 2-benzoxazolyl, C(O)N(H)Ph, or N(H)C(O)Ph, which are optionally substituted with from 1 to 4 substituents independently selected from $C_1$–$C_6$ alkyl, fluoro, chloro, bromo, iodo, nitro, $NHR_7$, $NR_7R_8$, and $OR_7$,
wherein $R_7$ and $R_8$ are independently H or $C_1$–$C_6$ alkyl;
wherein each hydrocarbyl or heterocyclic radical above is optionally substituted with from 1 to 3 substituents independently selected from halo, $C_1$–$C_6$ alkyl, $C_3$–$C_6$ cycloalkyl, $C_1$–$C_6$ alkenyl, $C_1$–$C_6$ alkynyl, phenyl, hydroxyl, amino, (amino)sulfonyl, N-acetyl, O-acetyl, $C_1$–$C_6$ thioalkyl, $C_1$–$C_6$ alkoxy, COOH, COO($C_1$–$C_6$ allyl), $SO_3Na$, $SO_3H$, $SO_2NH_2$, cyano, $CH_2NH_2$, acetyl, di($C_1$–$C_6$ alkyl)amino, and nitro, wherein the alkyl, cycloalkyl, alkenyl, alkynyl, and phenyl substituents may be optionally substituted with from 1 to 3 substituents independently selected from halo, $C_1$–$C_6$ alkyl, hydroxyl, amino, and nitro; and
pharmaceutically acceptable salts thereof.
Preferred are compounds of Formula II

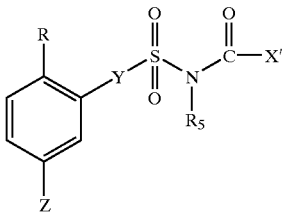

and pharmaceutically acceptable salts thereof, wherein X' is $OR_1$, $SR_1$, $NHR_1$, or $NR_1R_2$, and $R_1$, $R_2$, R, Z, Y, and $R_5$ are as defined above.

Also preferred are compounds of Formula III

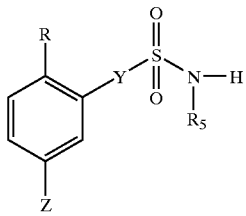

and pharmaceutically acceptable salts thereof, wherein R, Z, Y, and $R_5$ are as defined above.

Preferred are compounds of Formula IV

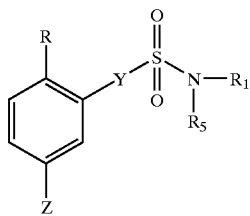

and pharmaceutically acceptable salts thereof, wherein $R_1$, R, Z, Y, and $R_5$ are as defined above.

Preferred is a compound of Formula I, and pharmaceutically acceptable salts thereof, wherein R is H or methyl.

Preferred is a compound of Formula I, and pharmaceutically acceptable salts thereof, wherein R is methyl.

Preferred is a compound of Formula I, and pharmaceutically acceptable salts thereof, wherein Z is as defined above for Formula I and is optionally substituted with from 1 to 4 substituents independently selected from fluoro, chloro, and methyl.

Preferred is a compound of Formula I, and pharmaceutically acceptable salts thereof, wherein Z is as defined above for Formula I and is substituted with from 1 to 3 substituents, wherein the substituents are as defined above for Formula I.

Preferred is a compound of Formula I, and pharmaceutically acceptable salts thereof, wherein Z is as defined above for Formula I and is substituted with from 1 to 3 substituents independently selected from fluoro, chloro, bromo, and iodo.

Preferred is a compound of Formula I, and pharmaceutically acceptable salts thereof, wherein Z is C(O)N(H)Ph.

Preferred is a compound of Formula I, and pharmaceutically acceptable salts thereof, wherein Z is C(O)N(H)Ph substituted with at least 1 fluoro.

Preferred is a compound of Formula I, and pharmaceutically acceptable salts thereof, wherein Z is C(O)N(H)Ph substituted with at least 2 fluoro groups.

Preferred is a compound of Formula I, and pharmaceutically acceptable salts thereof, wherein Z is C(O)N(O)Ph substituted with at least 2 fluoro groups, wherein the said at least 2 fluoro groups are bonded to adjacent carbon atoms.

Preferred is a compound of Formula I, and pharmaceutically acceptable salts thereof, wherein Z is (3,4-difluorophenyl)amino-carbonyl.

Preferred is a compound of Formula I, and pharmaceutically acceptable salts thereof, wherein Z comprises 2-indolyl optionally substituted with from 1 to 4 substituents independently selected from fluoro, chloro, and methyl.

Preferred is a compound of Formula I, and pharmaceutically acceptable salts thereof, wherein Z is 5,6-difluoro-indol-2-yl.

Preferred is a compound of Formula I, and pharmaceutically acceptable salts thereof, wherein $R_5$ is H.

Preferred is a compound of Formula I, and pharmaceutically acceptable salts thereof, wherein $R_5$ is a cation selected from an alkali earth metal cation, an alkaline earth metal cation, ammonium, and choline.

Preferred is a compound of Formula I, and pharmaceutically acceptable salts thereof, wherein $R_5$ is sodium cation, potassium cation, choline, or hemi calcium cation.

Preferred is a compound of Formula I, and pharmaceutically acceptable salts thereof, wherein W is $SO_2$.

Preferred is a compound of Formula I, and pharmaceutically acceptable salts thereof, wherein X is $R_1$, $OR_1$, $SR_1$, $NHR_1$, or $NR_1R_2$ wherein $R_1$ and $R_2$ are independently selected from $C_1$–$C_8$ alkyl $C_2$–$C_8$ alkenyl, $C_2$–$C_8$ alkynyl, benzyl, $C_3$–$C_6$ cycloalkyl, $C_2$–$C_6$ heterocyclic radical, and phenyl, wherein the alkyl, alkenyl, alkynyl, heterocyclic radical, benzyl, and phenyl groups are optionally substituted with from 1 to 3 independently selected substituents, wherein the substituents are as defined above for Formula I.

Preferred is a compound of Formula I, and pharmaceutically acceptable salts thereof, wherein X is $R_1$, $OR_1$, $NHR_1$, or $NR_1R_2$ wherein $R_1$ and $R_2$ are independently selected from $C_2$–$C_5$ alkyl, $C_2$–$C_5$ alkenyl, $C_2$–$C_5$ alkynyl, benzyl, and phenyl, wherein the alkyl, alkenyl, alkynyl, benzyl, and phenyl groups are optionally substituted with from 1 to 3 independently selected substituents, wherein the substituents are as defined above for Formula I.

Preferred is a compound of Formula I, and pharmaceutically acceptable salts thereof, wherein X is phenylamino, phenoxy, alkoxy, alkylamino, dialkylamino, or (carboxy) alkoxy.

Preferred compounds of the present invention are selected from the group consisting of:

Carbamic acid, [[[5-(5,6-difluoro-1H-indol-2-yl)-2-methoxyphenyl]amino]sulfonyl]-, dodecyl ester;

Carbamic acid, [[[5-[[(3,4-difluorophenyl)amino]carbonyl]-2-ethoxyphenyl]amino]-sulfonyl]-, 2-(4-morpholinyl)ethyl ester;

Carbamic acid, [[(5-[[(3,4-difluorophenyl)amino]carbonyl]-2-ethoxyphenyl]amino]-sulfonyl]-, 3-(dimethylamino) propyl ester;

Carbamic acid, [[[5-[[(3,4-difluorophenyl)amino]carbonyl]-2-ethoxyphenyl]amino]-sulfonyl]-, 2-(1-pyrrolidinyl)ethyl ester;

Carbamic acid, [[[5-[[(3,4-difluorophenyl)amino]carbonyl]-2-ethoxyphenyl]amino]-sulfonyl]-, 2-(dimethylamino)ethyl ester;

Carbamic acid, [[[5-[[(3,4-difluorophenyl)amino]carbonyl]-2-ethoxyphenyl]amino]-sulfonyl]-, 2-phenylethyl ester, monopotassium salt;

Carbamic acid, [[[5-[[(3,4-difluorophenyl)amino]carbonyl]-2-ethoxyphenyl]amino]-sulfonyl]-, 2-(2-thienyl)ethyl ester;

Carbamic acid, [[[5-[[(3,4-difluorophenyl)amino]carbonyl]-2-ethoxyphenyl]amino]-sulfonyl]-, 2-(ethylsulfonyl)ethyl ester;

Carbamic acid, [[[5-[[(3,4-difluorophenyl)amino]carbonyl]-2-ethoxyphenyl]amino]-sulfonyl]-, 3-bromopropyl ester;

Carbamic acid, [[[5-[[(3,4-difluorophenyl)amino]carbonyl]-2-ethoxyphenyl]amino]-sulfonyl]-, 2-[[(phenylmethoxy)carbonyl]amino] ethyl ester;

Carbamic acid, [[[5-[[(3,4-difluorophenyl)amino]carbonyl]-2-ethoxyphenyl]amino]-sulfonyl]-, 2-(3-thienyl) ethyl ester;

Carbamic acid, [[[5-(5,6-difluoro-1H-indol-2-yl)-2-methoxyphenyl]-amino]sulfonyl]-, octyl ester;

Carbamic acid, [[[(5-(5,6-difluoro-1H-indol-2-yl)2-methoxyphenyl]-amino]sulfonyl]-methyl-, 3-phenylmethoxy)propyl ester;
Carbamic acid, [[5-(5,6-difluoro-1H-indol-2-yl)-2-methoxyphenyl]-amino]sulfonyl]-(phenylmethyl)-, 3-(phenylmethoxy)propyl ester;
Carbamic acid, [[[5-(5,6-difluoro-1H-indol-2-yl)-2-methoxyphenyl]-amino]sulfonyl]-2-(dimethylamino)ethyl ester, monohydrochloride;
Acetic acid, [[[[[[5-(5,6-difluoro-1H-indol-2-yl)-2-methoxyphenyl]-amino]sulfonyl]-amino]carbonyl]oxy]-, phenylmethyl ester;
Benzamide, 3-[[[[[(3,5-dichlorophenyl)amino]carbonyl]amino]-sulfonyl]-amino]-N-(3,4-difluorophenyl)-4-methoxy-;
Benzamide, N-(3,4-difluorophenyl)-4-methoxy-3-[[[[(phenylamino)-carbonyl]amino]-sulfonyl]amino]-;
Carbamic acid, [[[5-[[(3,4-difluorophenyl)amino]carbonyl]-2-methoxyphenyl]amino]-sulfonyl]-, ethyl ester;
Benzamide, N-(3,4-difluorophenyl)-4-methoxy-3-[[[[[(4-methoxyphenyl)-amino]-sulfonyl]amino]carbonyl]amino]-;
Carbamic acid, [[[5-(5,6-difluoro-1H-indol-2-yl)-2-methoxyphenyl]-amino]sulfonyl]-, butyl ester;
Carbamic acid, [[[5-(5,6-difluoro-1H-indol-2-yl)-2-methoxyphenyl]-amino]sulfonyl]-, 2-methylpropyl ester;
Carbamic acid, [[(5-[[(3,4-difluorophenyl)amino]carbonyl]-2-methoxyphenyl]amino]-sulfonyl]-, 2-methylpropyl ester;
Urea, N-(3,5-dichlorophenyl)-]-N'-[[[5-(5,6-difluoro-1H-indol-2-yl)-2-methoxyphenyl]-amino]sulfonyl]-;
Carbamic acid, [[[5-(5,6-difluoro-1H-indol-2-yl)-2-methoxyphenyl]-amino]sulfonyl]-, ethyl ester;
Carbamic acid, [[[5-(1H-indol-2-yl)-2-methoxyphenyl]amino]sulfonyl]-, ethyl ester;
Urea, N-(4-chlorophenyl)-N'-[[[5-(5,6-difluoro-1H-indol-2-yl)-2-methoxyphenyl]-amino]sulfonyl]-;
Urea, N-[[[5-(5,6-difluoro-1H-indol-2-yl)-2-methoxyphenyl]-amino]sulfonyl]-N'-(4-methylphenyl)-;
Carbamic acid, [[[5-(5,6-difluoro-1H-indol-2-yl)-2-methoxyphenyl]-amino]sulfonyl]-methyl ester;
Carbamic acid, [[[5-(5,6-difluoro-1H-indol-2-yl)-2-methoxyphenyl]-amino]sulfonyl]-heptyl ester;
Carbamic acid, [[[5-(5,6-difluoro-1H-indol-2-yl)-2-methoxyphenyl]-amino]sulfonyl]-pentyl ester;
Carbamic acid, [[[5-(5,6-difluoro-1H-indol-2-yl)-2-methoxyphenyl]-amino]sulfonyl]-(2E)-3-phenyl-2-propenyl ester;
Carbamic acid, [[[5-[[(3,4-difluorophenyl)amino]carbonyl]-2-methoxyphenyl]amino]sulfonyl]-, (2E)-3-phenyl-2-propenyl ester;
Carbamic acid, [[[5-(5,6-difluoro-1H-indol-2-yl)-2-methoxyphenyl]-amino]sulfonyl]-2-(1-methylethoxy)ethyl ester;
Carbamic acid, [[[5-[[(3,4-difluorophenyl)amino]carbonyl]-2-methoxyphenyl]-amino]sulfonyl]-, 2-(1-methylethoxy)ethyl ester;
Carbamic acid, [[[5-(5,6-difluoro-1H-indol-2-yl)-2-methoxyphenyl]-amino]sulfonyl]-, phenylmethyl ester,
Sulfamide, N-[5-(5,6-difluoro-1H-indol-2-yl)-2-methoxyphenyl]-N'-methyl-;
Benzamide, N-(3,4-difluorophenyl)-4-methoxy-3-[[[(methylamino)-sulfonyl]amino]-;
Carbamic acid, [[[5-[[(3,4-difluorophenyl)amino]carbonyl]-2-methoxyphenyl]amino]-sulfonyl]-, 3-(4-pyridinyl)propyl ester;
Carbamic acid, [[[5-(5,6-difluoro-1H-indol-2-yl)-2-methoxyphenyl]-amino]sulfonyl]-2-phenylethyl ester;
Carbamic acid, [[[5-[[(3,4-difluorophenyl)amino]carbonyl]-2-methoxyphenyl]amino]-sulfonyl]-, 2-phenylethyl ester;
Carbamic acid, [[[5-[[(3,4-difluorophenyl)amino]carbonyl]-2-methoxyphenyl]amino]-sulfonyl]-, phenylmethyl ester,
Acetic acid, [[[[[[5-(5,6-difluoro-1H-indol-2-yl)-2-methoxyphenyl]-amino]sulfonyl[-amino]carbonyl]oxy]-, methyl ester,
Acetic acid, [[[[[[5-[[(3,4-difluorophenyl)amino]carbonyl]-2-methoxyphenyl]amino]-sulfonyl]amino]carbonyl]oxy]-, methyl ester;
Carbamic acid, [[[5-(5,6-difluoro-1H-indol-2-yl)-2-methoxyphenyl]-amino]sulfonyl]-3-hydroxypropyl ester;
Carbamic acid, [[[5-[[(3,4-difluorophenyl)amino]carbonyl]-2-methoxyphenyl]amino]-sulfonyl]-, 3-hydroxypropyl ester;
Carbamic acid, [[[5-(5,6-difluoro-1H-indol-2-yl)-2-methoxyphenyl]-amino]sulfonyl]-, 2-ethoxyethyl ester,
Carbamic acid, [[[5-[[(3,4-difluorophenyl)amino]carbonyl]-2-methoxyphenyl]amino]sulfonyl]-, 2-ethoxyethyl ester;
Carbamic acid, [[[5-(5,6-difluoro-1H-indol-2-yl)-2-methoxyphenyl]-amino]sulfonyl]-3-(phenylmethoxy)propyl ester,
Carbamic acid, [[[5-[[(3,4-difluorophenyl)amino]carbonyl]-2-methoxyphenyl]amino]-sulfonyl]-, 3-(phenylmethoxy)propyl ester;
Carbamic acid, [[[5-(5,6-difluoro-1H-indol-2-yl)-2-methoxyphenyl]-amino]sulfonyl]-hexyl ester,
Carbamic acid, [[[5-[[(3,4-difluorophenyl)amino]carbonyl]-2-methoxyphenyl]amino]-sulfonyl]-, hexyl ester;
Carbamic acid, [[[5-(5,6-difluoro-1H-indol-2-yl)-2-methoxyphenyl]-amino]sulfonyl]-, 1,1-dimethylethyl ester;
Sulfamide, [5-(5,6-difluoro-1H-indol-2-yl)-2-methoxyphenyl]-;
Benzamide, 3-[(aminosulfonyl)amino]-N-(3,4-difluorophenyl)-4-methoxy-;
Carbamic acid, [[[5-[[(3,4-difluorophenyl)amino]carbonyl]-2-methoxyphenyl]amino]-sulfonyl]-, 2-(1,3-dihydro-1,3-dioxo-2H-isoindol-2-yl) ethyl ester;
Benzamide, N-(3,4-difluorophenyl)-3-[[[[(dimethylamino)sulfonyl]-amino]carbonyl]-amino]-4-methoxy-;
Carbamic acid, [[[5-[[(3,4-difluorophenyl)amino]carbonyl]-2-methoxyphenyl]amino]-sulfonyl]-, 1,1-dimethylethyl ester;
Benzamide, N-(3,4-difluorophenyl)-3-[[[[[[4-(1,1-dimethylethyl)phenyl]-amino]carbonyl]amino]sulfonyl]amino]-4-methoxy-;
Benzamide, N-(3,4-difluorophenyl)-4-methoxy-3-[[[[(3-nitrophenyl)-amino]-carbonyl]amino]sulfonyl]amino]-;
Benzamide, 3-[[[[[(3-chlorophenyl)amino]carbonyl]amino]sulfonyl]-amino]-N-(3,4-difluorophenyl)-4-methoxy-;
Benzamide, 3-[[[[[[3,5-bis(trifluoromethyl)phenyl]amino]-carbonyl]amino]sulfonyl]-amino]-N-(3,4-difluorophenyl)-4-methoxy-;
Benzamide, 3-[[[[[(4-aminophenyl)amino]carbonyl]amino]-sulfonyl]amino]-N-(3,4-difluorophenyl)-4-methoxy-, mono(trifluoroacetate);
Benzamide, N-(3,4-difluorophenyl)-4-methoxy-3-[[[[[3-(trifluoromethyl)phenyl]-amino]carbonyl]-amino]sulfonyl]amino]-;
Benzoic acid, 4-[[[[[[5-[[(3,4-difluorophenyl)amino]carbonyl]-2-methoxyphenyl]-amino]sulfonyl]amino]carbonyl]amino]-;

Benzamide, N-(3,4-difluorophenyl)-4-methoxy-3-[[[[[(4-methoxyphenyl)-amino]-carbonyl]amino]sulfonyl]amino]-;

Benzamide, N-(3,4-difluorophenyl)-4-methoxy-3-[[[[(phenylamino)-carbonyl]-amino]sulfonyl]amino]-;

Benzamide, 3-[[[[[(4-chlorophenyl)amino]carbonyl]amino]sulfonyl]-amino]-N-(3,4-difluorophenyl)-4-methoxy-; and Carbamic acid, [[[5-[[(3,4-difluorophenyl)amino]carbonyl]-2-methoxyphenyl]amino]sulfonyl]methyl-, ethyl ester.

The invention also provides pharmaceutical compositions, comprising compounds of Formula I, and pharmaceutically acceptable salts thereof, in admixture with a pharmaceutically acceptable carrier, diluent, or excipient. Preferred compositions comprise a compound of Formulas II through IV with a pharmaceutically acceptable carrier.

The compounds of Formula I and their pharmaceutically acceptable salts are useful for treating diseases responsive to inhibition of 15-LO, including atherosclerosis, diseases involving chemotaxis of monocytes, inflammation, stroke, coronary artery disease, asthma, arthritis, including osteoarthritis and rheumatoid arthritis, colorectal cancer, and psoriasis. Thus, the invention also provides methods for treating mammals with diseases relating to the 15-LO cascade. These methods are for treating, preventing, or ameliorating the related condition or disease. These methods include the following.

A method for inhibiting 15-LO, said method comprising administering to a patient in need of 15-lipoxygenase inhibition a pharmaceutically-effective amount of a compound of Formula I, or a pharmaceutically acceptable salt thereof.

A method for treating or preventing atherosclerosis, said method comprising administering to a patient at risk or in need of such treatment a therapeutically-effective amount of a compound of Formula I, or a pharmaceutically acceptable salt thereof.

A method for inhibiting the chemotaxis of monocytes, said method comprising administering to a patient in need of inhibition of monocytic migration a therapeutically-effective amount of a compound of Formula I, or a pharmaceutically acceptable salt thereof.

A method for treating or preventing inflammation, said method comprising administering to patient at risk or in need of such treatment a therapeutically-effective amount of a compound of Formula I, or a pharmaceutically acceptable salt thereof.

A method for treating or preventing stroke, said method comprising administering to a patient at risk or in need of such treatment a therapeutically-effective amount of a compound of Formula I, or a pharmaceutically acceptable salt thereof.

A method for treating or preventing coronary artery disease, said method comprising administering to a patient at risk or in need of such treatment a therapeutically-effective amount of a compound of Formula I, or a pharmaceutically acceptable salt thereof.

A method for treating or preventing asthma, said method comprising administering to patient at risk or in need of such treatment a therapeutically-effective amount of a compound of Formula I, or a pharmaceutically acceptable salt thereof.

A method for treating or preventing arthritis, said method comprising administering to patient at risk or in need of such treatment a therapeutically-effective amount of a compound of Formula I, or a pharmaceutically acceptable salt thereof.

A method for treating or preventing colorectal cancer, said method comprising administering to a patient at risk or in need of such treatment a therapeutically-effective amount of a compound of Formula I, or a pharmaceutically acceptable salt thereof.

A method for treating or preventing psoriasis, said method comprising administering to a patient at risk or in need of such treatment a therapeutically-effective amount of a compound of Formula I, or a pharmaceutically acceptable salt thereof.

Other aspects and features of the invention will be apparent from the disclosure, examples, and claims set forth below.

DETAILED DESCRIPTION OF THE INVENTION

The invention provides compounds of Formula I, compositions containing the compounds, methods of making the compounds, and methods of using the compounds to treat diseases responsive to inhibition of 15-LO. Other features of the invention, and preferred embodiments thereof, will become apparent from the examples and claims below.

A. Terms

Certain terms used herein are defined below and by their usage throughout this disclosure.

Alkyl groups include aliphatic (i.e., hydrocarbon radicals containing hydrogen and carbon atoms) with a free valence. Alkyl groups are understood to include straight chain and branched structures. Preferred alkyl groups have from 1 to 6 carbon atoms. Examples of typical alkyl groups include methyl, ethyl, propyl, isopropyl, butyl, n-butyl isobutyl, t-butyl, pentyl, isopentyl, 2,3-dimethylpropyl, hexyl, 2,3-dimethyl hexyl, 1,1-dimethylpentyl, heptyl, and octyl. Cycloalkyl groups are $C_3$–$C_8$ cyclic structures, examples of which include cyclopropyl, cyclobutyl, cyclopentyl, cyclohexyl, and cyclooctyl.

Alkyl and cycloalkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, (heterocyclic radical)oxy, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, $CH_2NH_2$, acetyl, trifluoromethyl, and nitro. Specific examples include COOH, thiomethyl, methoxy, ethoxy, dimethylamino, ethylmethylamino, diethylamino, and chloro. Other examples include fluoromethyl, hydroxyethyl, 2,3-dihydroxyethyl, (2- or 3-furanyl)methyl, cyclopropylmethyl, methylcyclopropyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, 2-ethoxycyclopentyl, N-pyridinylethyl, diethylaminoethyl, and cyclobutylmethyl.

Alkenyl groups are analogous to alkyl groups, but have at least one double-bond (two adjacent $sp^2$ carbon atoms). Depending on the placement of a double-bond and substituents, if any, the geometry of the double-bond may be entgegen (E), zusammen (Z), cis, or trans. Similarly, alkynyl groups have at least one triple-bond (two adjacent sp carbon atoms). Unsaturated alkenyl or alkenyl groups may have one or more double- or triple-bonds, respectively, or a mixture thereof; like alkyl groups, they may be straight chain or branched, and they may be substituted as described above and throughout the disclosure. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4hydroxy-3-butynyl, 3-(3-fluorophenyl)-2-propynyl, and 2-methyl-2-propenyl.

The foregoing groups are referred to collectively as "hydrocarbyl" groups. More general forms of substituted hydrocarbyls include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to Formula I, therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl and so on. Where $R_1$ is phenyl, for example, $R_1$ thus includes 3-halo-4-hydroxyphenyl, 3-(fluoro or chloro)-4-nitrophenyl 3,4-dichlorophenyl, 3,5-dichlorophenyl, 3,5-difluorophenyl, 3-hydroxy-4-nitrophenyl, 4-hydroxy-3-nitrophenyl, 3-chlorophenyl, 4-chlorophenyl, 2-fluorophenyl, 3-fluorophenyl, 4-fluorophenyl, 3,4-difluorophenyl, 2,3-difluorophenyl-2,4-difluorophenyl, 3-trifluoromethylphenyl, 4-trifluoromethylphenyl, 3-aminophenyl, 4-aminophenyl, 3,5-dimethylphenyl, 3-methylphenyl, 4-methylphenyl, 3-nitrophenyl, 4-nitrophenyl, 3-nitro-4-chlorophenyl, 3-cyanophenyl, 4-cyanophenyl, 3-methyleneaminophenyl, 4-methyleneaminophenyl, 3-hydroxyphenyl, 4-hydroxyphenyl, 3,4-dihydroxyphenyl, 4chloro-3-trifluoromethylphenyl, 3-carbomethoxyphenyl, 4-carbomethoxyphenyl, bis(3,5-trifluoromethyl)phenyl, 4-t-butylphenyl, 4-n-butylphenyl, 4-isopropylphenyl, 3-acetylphenyl, 4-sulfonic acid (e.g., sodium salt), 3-carboxyphenyl, 4carboxyphenyl, 3-methoxyphenyl, 4-methoxyphenyl, 3,4-dimethoxyphenyl, 4-acetamidophenyl, 3-amino-4-halophenyl, 3-alkoxy-4-halophenyl, 3-halo-4-alkylaminophenyl, 4-(N,N-dimethylamino)phenyl, 3-cycloalkylphenyl, 3(3',5'-dihalophenyl)-4-nitrophenyl, 4-aryloxyphenyl, arylalkyloxyphenyl, heterocyclic radical phenyl, (heterocyclic radical)oxy, 4-sulfamoylphenyl (or 4-aminosulfonylphenyl), 3-(alkylcarbonyloxy)phenyl such as 3-acetylphenyl, and 3-($C_1$–$C_4$ thioalkyl)phenyl. It also follow that where Z includes a phenyl, such as Z=NH(CO)Ph, the phenyl can be similarly substituted.

Similarly, the invention features analogous examples of substituted R where R is a heterocyclic radical. Heterocyclic radicals, which include but are not limited to heteroaryls, include cyclic and bicyclic ring moieties having between 1 and 4 heteroatoms selected independently from O, S, and N, and having from 2 to 11 carbon atoms. The rings may be aromatic or nonaromatic, with $sp^2$ or $sp^3$ carbon atoms. Examples include: furyl, oxazolyl, isoxazolyl, thienyl, thiophenyl, thiazolyl, pyrrolyl, imidazolyl, triazolyl such as 1,3,4-triazolyl, tetrazolyl, thiazolyl, oxazolyl, xanthenyl, pyronyl, pyridyl, pyrimidyl, triazinyl, pyrazinyl, pyridazinyl, indolyl, and pyrazolyl. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl. Particularly preferred heterocyclic radicals include 2-pyridyl, 3-pyridyl, 4pyridyl, 3-picolinyl, 2-thienyl, 3-thienyl, 2-furyl, 3-furyl, dansyl, 8-quinoyl, 2-acetamido-4-thiazole, and imidazolyl. These may be substituted with one or more substituents such as halo, $C_1$–$C_4$ alkoxy, $COOR_6$, $SO_3Na$, $SO_3H$, $SO_2NH_2$, cyano, $CH_2NH_2$, acetyl, trifluoromethyl. Examples of substituted heterocyclic radicals include chloropyranyl, methylthienyl, fluoropyridyl, amino-1-,4-benzisoxazinyl, nitroisoquinolinyl, and hydroxyindolyl. Heterocyclic radicals can be bonded through a carbon atom or a heteroatom.

The term "patient" means a mammal such as a human or a domestic animal such as a dog, cat, horse, bovine, porcine, and sheep.

The term "effective amount" means that quantity of a compound of Formula I that inhibits the 15-LO enzyme in a patient to an extent that results in prevention or treatment of an inflammatory condition or otherwise benefits a patient by virtue of having endogenous 15-LO enzymes inhibited.

The term "halo" includes fluoro, chloro, bromo, and iodo.

The term "amino" means $NH_2$.

The term "alkylamino" means an alkyl group as defined above bonded through an —NH— group.

The term "dialkylamino" means two alkyl groups, each bonded through an —N— group.

The phrase "pharmaceutically acceptable cation" means an alkali or alkaline earth metal cation or a protonated organic amine.

B. Compounds

The invention provides compounds of Formula I and pharmaceutically acceptable salts thereof. Also provided are hydrates and solvated forms thereof; masked or protected forms; and racemic mixtures, or enantiomerically or optically pure forms (at least 90%, and preferably 95%, 98% or greater purity).

Pharmaceutically acceptable salts include carboxylate salts (e.g., $C_1$–$C_8$ alkyl, cycloalkyl, aryl, heteroaryl, or heterocyclic) and amino acid addition salts which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as nontoxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.*, 1977;66:1–19, which is incorporated herein by reference.

C. Synthesis

The compounds of the present invention can be synthesized according to the synthetic routes outlined in Schemes 1–4. Scheme 1 illustrates the preparation of compounds of the present invention of Formula Ia, which is a compound of Formula I wherein W is $SO_2$, V is C=O, $R_5$ is hydrogen, X is $OR_1$, $SR_1$, $NHR_1$, or $NR_1R_2$, and $R_1$, $R_2$, R, Z, and Y are as defined above for Formula I. In Scheme 1, chlorosulfonylisocyanate of formula (1) (CSI), is reacted with either an alcohol, thiol, or amine of formula H—X', wherein X' is $OR_1$, $SR_1$, or $NHR_1$ or $NR_1R_2$, respectively, wherein $R_1$ and $R_2$ are as defined above, in a nonprotic solvent such as methylene chloride, which can contain, but does not require, an amine such as, for example, an organic tertiary amine or pyridine, to give a chlorosulfonamide of formula (2). The chlorosulfonamide of formula (2) is then further reacted with an alcohol or amine of formula (3) wherein Y' is OH or $NH_2$, in an organic solvent such as methylene chloride with an amine base such as triethyl amine or pyridine to give a compound of Formula Ia.

Scheme 2 illustrates the preparation of a compound of the present invention of Formula Ib, which is a compound of Formula I wherein W is $SO_2$, V is C=O, X is $OR_1$, $SR_1$, $NHR_1$, or $NR_1R_2$, and $R_1$, $R_2$, R, Z, Y, and $R_5$ are as defined above for Formula I. Scheme 2 further illustrates the preparation of a compound of the present invention of Formula Ic, which is a compound of Formula I wherein W is $SO_2$, —V— is a covalent bond, X is hydrogen, and R, Z, Y, and $R_5$ are as defined above for Formula I. In Scheme 2, a compound of Formula Ia is reacted with an organic base, such as 1,8-diazabicyclo[5.4.0]undec-7-ene (DBU), in a nonprotic solvent, such as methylene chloride, and alkylated with an alkyl halide of formula $R_5$-L, wherein L is chloro, bromo, or iodo, to give a compound of Formula Ib. A compound of Formula Ib, wherein X' is $OR_1$, wherein $R_1$ is an acid labile group such as, for example, tert-butyl or a hydrogenolysis labile group such as benzyl, can further be converted to a compound of Formula Ic by acid-catalyzed cleavage or hydrogenolysis. For example, when $R_1$ is tert-butyl, the reaction can be carried out by treating a compound of Formula Ib wherein X' is $OR_1$, with hydrogen chloride gas or trifluoroacetic acid (TFA) in a solvent such as methylene chloride. Alternatively, when $R_1$ is benzyl, the reaction can be carried out by treating a compound of Formula Ib wherein X' is $OR_1$, with hydrogen gas in the presence of a suitable hydrogenation catalyst such as palladium (0) tetrakis (triphenyl)-phosphine in a suitable solvent such as ethanol, tetrahydrofuran (THF), or acetic acid.

Compounds of the present invention of Formula Id, which is a compound of Formula I wherein —V— is a covalent bond, W is $SO_2$, X is $R_1$, and R, Z, Y, and $R_5$ are as defined above for Formula I, can be synthesized according to the method illustrate in Scheme 3. In Scheme 3, a compound of formula (3), wherein Y' is OH or $NH_2$, is allowed to react with a sulfamylchloride of formula (4), wherein $R_1$ and $R_5$ are as defined above for Formula I, in an organic solvent such as acetonitrile with or without an organic base to give a compound of Formula Id.

Amines of formula (3), wherein Y' is $NH_2$ in Schemes 1 and 3 can be synthesized according to the methods described in WO 99/32433, which is hereby incorporated by reference. In particular, the procedure of Example 15 of WO 99/32433 may be used. Additional amines of formula (3), wherein Y' is $NH_2$, R is methoxy, and Z is optionally substituted indol-2-yl wherein the substituents are as defined above for Z in Formula I, can be synthesized according to the method illustrated in Scheme 4. In Scheme 4, a phenylacetic acid of formula (5) is converted to an acid chloride with a chlorinating reagent such as thionyl chloride or oxalyl chloride, which is then reacted with anisole in the presence of a Friedel-Crafts catalyst such as aluminum chloride to give a ketone of formula (6). The ketone of formula (6) is then subjected to dinitration using a nitrating reagent such as fuming nitric acid in acetic acid to give a compound of formula (7). The compound of formula (7) is then reduced using a reducing agent such as lithium aluminum hydride or hydrogen and a heavy metal catalyst such as Raney Ni, to give an intermediate di-amine, which undergoes an intermolecular cyclization to give an amino-indole of formula (8), which is the amine of formula (3) described immediately above wherein R' is the substituents described above for Z of Formula I.

Scheme 1

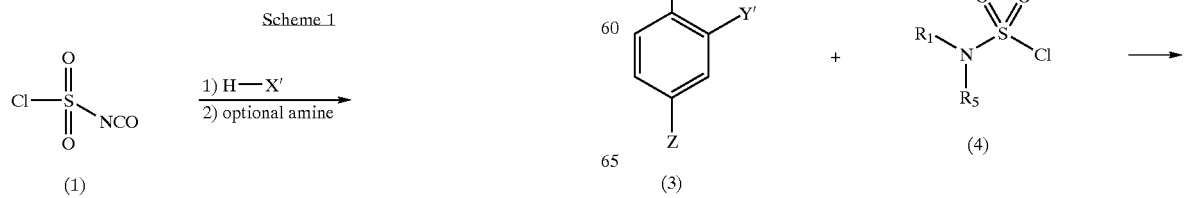

Scheme 2

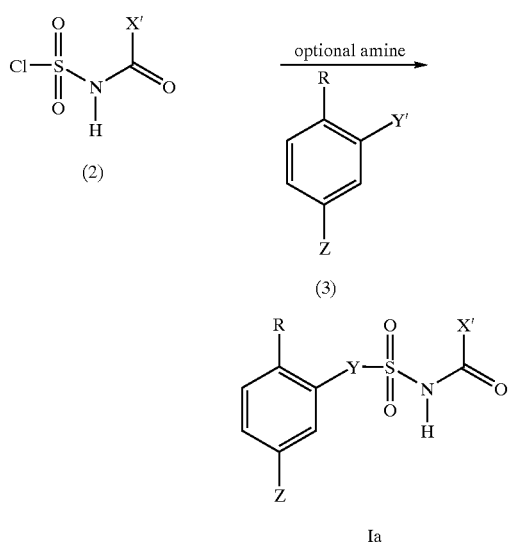

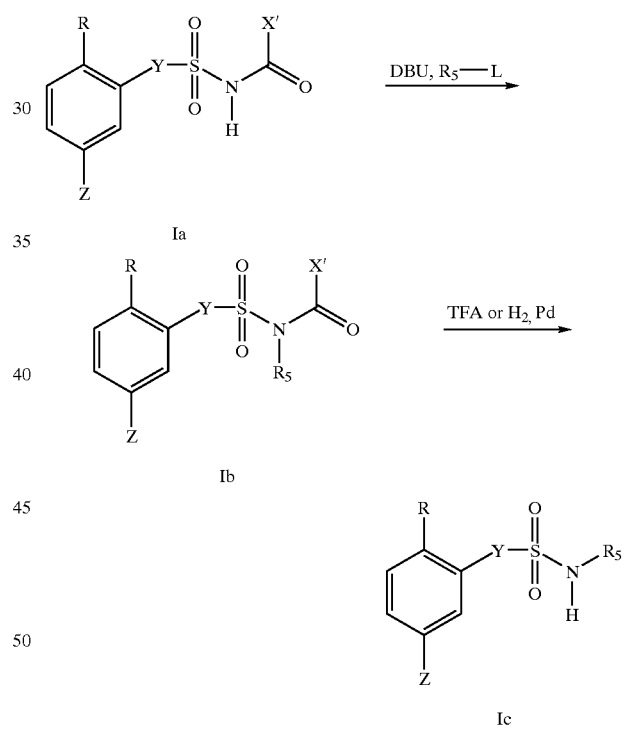

Scheme 3

-continued

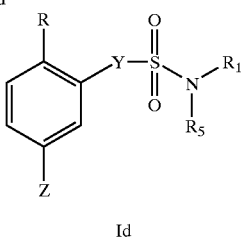

Id

Scheme 4

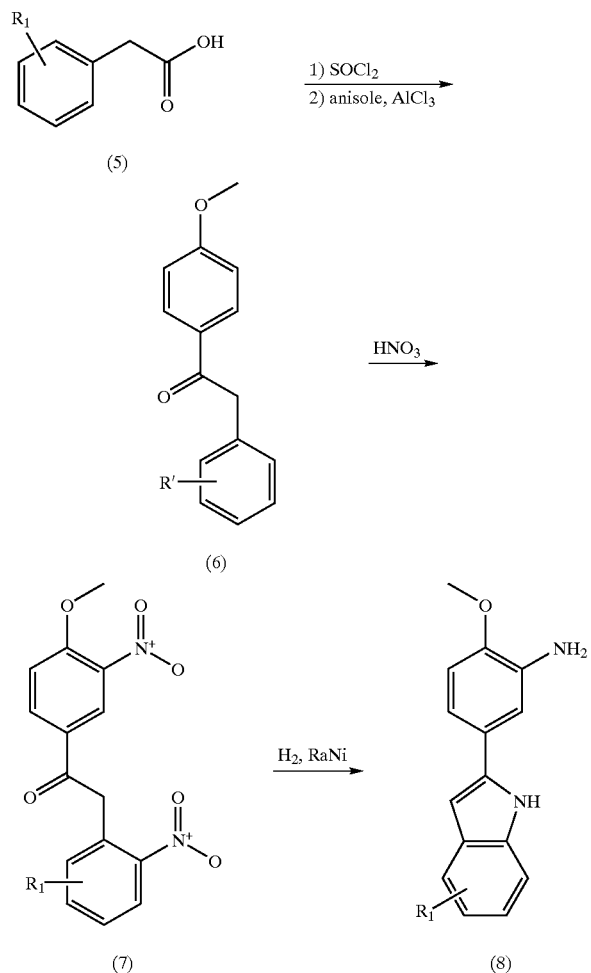

Further guidance and exemplification regarding the synthesis of the compounds of the present invention is provided in the chemical synthetic Examples 1 through 69 below.

The invention also includes disclosed compounds having one or more functional groups (e.g., hydroxyl, amino, or carboxyl) which may be masked by a protecting group so as to avoid unwanted side reactions. Some of these masked or protected compounds are pharmaceutically acceptable; others will be useful as intermediates. The use of protecting groups is fully described by Greene and Wuts in "Protecting Groups in Organic Synthesis" (John Wiley & Sons, $2^{nd}$ ed.).

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

The invention is further described in the working examples described below. The examples are provided for illustration only, and are not to be construed as limiting the invention in any respect As shown by Examples 1 and 25 described below, compounds of Formulas Ia and Ib may be prepared by reaction of a penultimate reactive sulfonyl-carbamic acid ester derivative such as a chlorosulfonamide of formula (2) or a trialkylamino sulfonyl carbamic acid ester, which is a zwitterionic compound wherein the chloro of the compound of formula (2) has been replaced by a trialkylammonium group and the nitrogen of the carbamic acid ester has been deprotonated. These reactive sulfonyl-carbamic acid ester derivatives may optionally be prepared in situ or isolated and purified before reaction with an amine of formula (3) wherein Y' is $NH_2$.

D. EXAMPLES

Example 1

Carbamic Acid, [[[5-(5,6-difluoro-IH-indol-2-yl)-2-methoxyphenyl]amino]-sulfonyl]-, Dodecyl Ester In methylene chloride (40 mL) was stirred chlorosulfonyl isocyanate (CSI) (1.56 g, 11 mmol). To this solution was added dodecanol (1.86 g, 10 mmol), in parts. The solution was stirred for 15 minutes. To this solution was added triethylamine (1.5 g, 15 mmol), and the mixture stirred an additional 15 minutes. To this was added 5-(5,6-difluoro-1H-indol-2-yl)-2-methoxy-phenylamine (2.33 g, 8.5 mmol), and the mixture stirred at room temperature for 24 hours. The mixture was washed with water (2×100 mL), and the organic phase dried over magnesium sulfate. The solvents were evaporated at reduced pressure to give a foam. The foam was dissolved in fresh methylene chloride (40 mL), and the solution was treated with 1N hydrochloric acid (40 mL). The resulting mixture was vigorously stirred for 20 minutes and then filtered to collect the solid. The solid was stirred into acetonitrile (40 mL) and filtered to collect the solid. The solid was then washed with a mixture of water-:acetonitrile (1:1) (10 mL) and dried at 65° C. to give 0.495 g of pure carbamic acid, [[[5-(5,6-difluoro-IH-indol-2-yl)-2-methoxyphenyl]amino]-sulfonyl]-, dodecyl ester. $^1$HNMR (DMSO-$d_6$) δ 0.80–0.84 (t, 3H), 1.14–1.21 (m, 18H), 1.4–1.55 (m, 2H), 3.78 (s, 3H), 4.00–4.05 (m, 2H), 6.75 (s, 1H), 7.12–7.18 (m, 1H), 7.23–7.31 (m, 1H), 7.41–7.48 (m, 1H), 7.60–7.70 (m, 2H), 9.25 (s, 1H), 11.40 (s, 1H), 11.61 (s, 1H) ppm Microanalysis: $C_{28}H_{37}F_2N_3O_5S$; calculated: C=59.45; H=6.59; N=7.43. found: C=59.46; H=6.81; N=7.32. MS: M$^+$+1=566 Da.

Example 2

Carbamic Acid, [[[5[[(3,4-difluorophenyl)amino] carbonyl]-2-methoxyphenyl]-amino]sulfonyl]-, 2-(4morpholinyl)ethyl ester The title compound was synthesized in the same manner as Example 1 using 2-morpholinylethanol (1.30 g, 10.0 mmol), CSI (1.56 g, 11.0 mmol), and 3-amino-N-(3,4-difluoro-phenyl)-4-methoxy-benzamide (1.95 g, 7.0 mmol) to give 0.270 g of pure carbamic acid, [[[5-[[(3,4-difluorophenyl)amino]carbonyl]-2-methoxyphenyl]amino] sulfonyl]-, 2-(4-morpholinyl)ethyl ester. $^1$HNMR (DMSO-$d_6$) δ 2.6–2.75 (m, 4H), 2.75–2.85 (m, 2H), 3.55–3.61 (m, 4H), 3.84 (s, 3H), 4.12–4.23 (m, 2H), 7.12–7.15 (d, 1H), 7.36–7.44 (m, 1H), 7.50–7.53 (m, 1H), 7.72–7.75 (m, 1H), 7.88–7.94 (m, 2H), 8.6–8.8 (br. s, 1H), 10.29 (s, 1H) ppm.

Microanalysis: $C_{21}H_{24}F_2N_4O_7S \cdot 0.22\ H_2O$; calculated: C=45.51; H=5.17; N=10.11. found: C=45.69; H=5.01; N=10.03. MS: $M^++1=515.3$ Da.

Example 3

Carbamic Acid, [[(5-[[(3,4-diflu rophenyl)amino]carbonyl]-2-methoxyphenyl]amino]sulfonyl]-, 3-(dimethylamino)propyl Ester The title compound was synthesized in the same manner as Example 1 using 2-dimethylaminopropanol (1.03 g, 10.0 mmol), CSI (1.56 g, 11.0 mmol), and 3-amino-N-(3,4-difluoro-phenyl)-4-methoxy-benzamide (1.95 g, 7.0 mmol) to give 0.505 g of pure carbamic acid, [[(5-[[(3,4-difluorophenyl)amino]carbonyl]-2-methoxyphenyl]amino]-sulfonyl]-, 3-(dimethylamino) propyl ester. $^1$HNMR (DMSO-d$_6$) δ 1.76–1.83 (m, 2H), 2.68 (s, 6H), 2.95–2.99 (m, 2H), 3.80–3.83 (m, 2H), 3.85 (s, 3H), 7.02–7.05 (d, 1H), 7.36–7.43 (m, 1H), 7.50–7.53 (m, 2H), 7.60–7.70 (br. S, 1H), 7.87–7.93 (m, 1H), 7.99–8.00 (m, 1H), 10.25 (s, 1H) ppm. Microanalysis: $C_{20}H_{24}F_2N_4O_6S \cdot 0.25H_2O$; calculated: C=48.92; H=5.03; N=11.41. found: C=48.85; H=4.84; N=11.41. MS: $M^++1=487.3$ Da.

Example 4

Carbamic Acid, [[[5-[[(3,4-difluorophenyl)amino]carbonyl]-2-methoxyphenyl]amino]-sulfonyl]-, 2-(1-pyrrolidinyl)ethyl ester The title compound was synthesized in the same manner as Example 1 using 2-pyrrolidinylethanol (1.15 g, 10.0 mmol), CSI (1.56 g, 11.0 mmol), and 3-amino-N-(3,4-difluoro-phenyl)-4-methoxy-benzamide (1.95 g, 7.0 mmol) to give 0.305 g of pure carbamic acid, [[[5-[[(3,4-difluorophenyl)amino]carbonyl]-2-methoxyphenyl]amino]-sulfonyl]-, 2-(1-pyrrolidinyl)ethyl ester. $^1$HNMR (DMSO-d$_6$) δ 1.79–1.9 (m, 1H), 3.11–3.38 (m, 6H), 3.86 (s, 3H), 4.00–4.05 (m, 2H), 7.03–7.05 (d, 1H), 7.36–7.43 (m, 1H), 7.50–7.65 (m, 3H), 7.87–7.93 (m, 1H), 8.00 (s, 1H), 10.26 (s, 1H) ppm Microanalysis: $C_{21}H_{24}F_2N_4O_6S \cdot 1.0H_2O$; calculated: C=48.83; H=5.07; N=10.85. found: C=49.13; H=4.90; N=10.72. MS: $M^++1=499.3$ Da.

Example 5

Carbamic Acid, [[[5-[[(3,4-difluorophenyl)amino]carbonyl]-2-methoxyphenyl]amino]sulfonyl]-, 2-(dimethylamino)ethyl ester The title compound was synthesied in the same manner as Example 1 using 2dimethylaminoethanol (0.89 g, 10.0 mmol), CSI (1.56 g, 11.0 mmol), and 3-amino-N-(3,4-difluorophenyl)-4-methoxy-benzamide (1.95 g, 7.0 mmol) to give 0.499 g of pure carbamic acid, [[[5-[[(3,4-difluorophenyl)amino]carbonyl]-2-methoxyphenyl]amino]sulfonyl]-, 2-(dimethylamino)ethyl ester. $^1$HNMR (DMSO-d$_6$) δ 2.68 (s, 6H), 3.17–3.32 (m, 2H), 3.87 (s, 3H), 4.05–4.10 (m, 2H), 7.04–7.06 (d, 1H), 7.36–7.50 (m, 1H), 7.52–7.58 (m, 2H), 7.55–7.65 (br. s, 1H), 7.88–7.93 (m, 1H), 8.00 (s, 1H), 10.26 (s, 1H) ppm. Microanalysis: $C_{19}H_{22}F_2N_4O_6S \cdot 0.4H_2O$; calculated: C=47.57; H=4.79; N=11.68. found: C=47.75; H=4.62; N=11.51. $MS^++1=473.3$ Da.

Example 6

Carbamic Acid, [[[5-[[(3,4-difluorophenyl)amino]carbonyl]-2-methoxyphenyl]amino]sulfonyl]-, 2-phenylethyl Ester, Monopotassium Salt To carbamic acid, [[[5-[[(3,4-difluorophenyl)amino]carbonyl]-2-methoxyphenyl]amino]sulfonyl]-, 2-phenylethyl ester (480 mg, 0.949 mmol) in acetonitrile (40 mL) was added KOH (1.90 mL of a 0.498N solution) in methanol. The mixture was stirred at room temperature for 15 minutes and evaporated in vacuo. The residue was triturated with ether (25 mL) and filtered to collect the solid which was dried at 65° C. in vacuo for 3 hours. This gave 0.490 g of the pure carbamic acid, [[[5-[[(3,4-difluorophenyl)amino]carbonyl]-2-methoxyphenyl]amino]sulfonyl]-, 2-phenylethyl ester, monopotassium salt. $^1$HNMR (DMSO-d$_6$) δ 2.67–2.71 (m, 2H), 3.83 (s, 3H), 3.86–3.90 (m, 2H), 6.99–7.02 (d, 1H), 7.10–7.25 (m, 5H), 7.35–7.55 (m, 2H), 7.64 (s, 1H), 7.82–7.93 (m, 1H), 8.00 (s, 1H), 10.23 (s, 1H) ppm. Microanalysis: $C_{23}H_{20}F_2N_4O_6SK \cdot 0.5H_2O$; calculated: C=49.99; H=3.83; N=7.60. found: C=49.71; H=3.82; N=7.65. MS: $M^++1=506.2$ Da.

Example 7

Carbamic Acid, [[[5-[[(3,4-difluorophenyl)amino]carbonyl]-2-methoxyphenyl]amino]sulfonyl]-, 2-(2-thienyl)ethyl ester The title compound was synthesized in the same manner as Example 1 using 2-(2-hydroxyethyl)thiophene (1.28 g, 10.0 mmol), CSI (1.56 g, 11.0 mmol), and 3-amino-N-(3, 4-difluoro-phenyl)-4-methoxy-benzamide (1.95 g, 7.0 mmol) to give 0.955 g of pure carbamic acid, [[[5-[[(3,4-difluorophenyl)amino]carbonyl]-2-methoxyphenyl]amino]sulfonyl]-, 2-(2-thienyl)ethyl ester. $^1$HNMR (DMSO-6) δ 3.07–3.10 (m, 2H), 3.79 (s, 3H), 4.22–4.26 (m, 2H), 6.88–6.92 (m, 2H), 7.16–7.18 (d, 1H), 7.30–7.31 (m, 1H), 7.36–7.44 (m, 1H), 7.50–7.53 (m, 1H), 7.85–7.93 (m, 3H), 9.44 (s, 1H), 10.32 (s, 1H), 11.50 (s, 1H) ppm. Microanalysis: $C_{21}H_{19}F_2N_3O_6S_2 \cdot 0.1H_2O$; calculated: C=49.13; H=3.77; N=8.19; found: C=48.87; H=3.91; N=8.10. MS: $M^++1=512.2$ Da.

Example 8

Carbamic Acid, [[[5-[[(3,4-difluorophenyl)amino]carbonyl]-2-methoxyphenyl]amino]sulfonyl]-, 2-(ethylsulfonyl)ethyl ester The title compound was synthesized in the same manner as Example 1 using 2-ethanesulfonyletanol (1.38 g, 10.0 mmol), CSI (1.56 g, 11.0 mmol), and 3-amino-N-(3,4-difluoro-phenyl)-4-methoxy-benzamide (1.95 g, 7.0 mmol), to give 2.05 g of pure carbamic acid, [[[5-[[(3,4-difluorophenyl)amino]carbonyl]-2-methoxyphenyl]amino]sulfonyl]-, 2-(ethylsulfonyl)ethyl ester. $^1$HNMR (DMSO-d$_6$) δ 1.13–1.17 (m, 3H), 3.08–3.13 (m, 2H), 3.40–3.50 (m, 2H), 3.84 (s, 3H), 4.38–4.41 (m, 2H), 7.19–7.21 (d, 1H), 7.37–7.51 (m, 2H), 7.89–7.94 (m, 3H), 9.60 (s, 1H), 10.33 (s, 1H), 11.59 (s, 1H) ppm. Microanalysis: $C_{19}H_{21}F_2N_3O_8S_2 \cdot 0.15H_2O$; calculated: C=43.53; H=4.10; N=8.02; found: C=43.50; H=4.09; N=8.01. MS: $M^++1=522.2$ Da.

Example 9

Carbamic Acid, [[[5-[[(3,4-difluorophenyl)amino]carbonyl]-2-methoxyphenyl]amino]sulfonyl]-, 3-bromopropyl ester The title compound was synthesized in the same manner as Example 1 using 3-bromopropanol (1.39 g, 10.0 mmol), CSI (1.56 g, 11.0 mmol), and 3-amino-N-(3,4-difluorophenyl)-4-methoxy-benzamide (1.95 g, 7.0 mmol) to give 0.495 g of pure carbamic acid, [[[5-[[(3,4-difluorophenyl)

amino]carbonyl]-2-methoxyphenyl]amino]sulfonyl]-, 3-bromopropyl ester. $^1$HNMR (DMSO-d$_6$) δ 2.06–2.13 (m, 2H), 3.51–3.54 (m, 2H), 3.84 (s, 3H), 4.14–4.17 (m, 2H), 7.18–7.21 (d, 1H), 7.37–7.53 (m, 2H), 7.86–7.94 (m, 3H), 9.53 (s, 1H), 10.32 (s, 1H), 11.40 (s, 1H) ppm. Microanalysis: $C_{18}H_{18}F_2BrN_3O_6S$; calculated: C=41.39; H=3.47; N=8.04. found: C=41.60; H=3.44; N=7.99. MS: M$^+$+1= 524.2 Da.

Example 10

Carbamic Acid, [[[5-[[(3,4-difluorophenyl)amino] carbonyl]-2-methoxyphenyl]amino]sulfonyl]-, 2-[[(phenylmethoxy)carbonyl]amino]ethyl ester The title compound was synthesized in the same manner as Example 1 using (2-hydroxyethyl)carbamic acid benzyl-lester (1.95 g, 10.0 mmol), CSI (1.56 g, 11.0 mmol), and 3-amino-N-(3,4-difluoro-phenyl)-4-methoxy-benzamide (1.95 g, 7.0 mmol) to give 0.639 g of pure carbamic acid, [[[5-[[(3,4-difluorophenyl)amino]carbonyl]-2-methoxyphenyl]amino]sulfonyl]-, 2-[[(phenylmethoxy)carbonyl]amino]ethyl ester. $^1$HNMR (DMSO-d$_6$) δ 3.26–3.33 (m, 2H), 3.81 (s, 3H), 4.07–4.09 (m, 2H), 4.98 (s, 2H), 7.16–7.18 (d, 1H), 7.28–7.44 (m, 7H), 7.50–7.53 (m, 1H), 7.86–7.94 (m, 3H), 9.45 (s, 1H), 10.32 (s, 1H), 11.40 (s, 1H) ppm. Microanalysis: $C_{25}H_{24}F_2N_4O_8S$. $_{0.2}H_2O$; calculated: C=51.53; H=4.22; N=9.62. found: C=51.15; H=4.08; N=9.51. MS: M$^+$+1=579.3 Da.

Example 11

Carbamic Acid, [[[5-[[(3,4-difluorophenyl)amino] carbonyl]-2-methoxyphenyl]amino]sulfonyl]-, 2-(3-thienyl)ethyl ester The title compound was synthesized in the same manner as Example 1 using 3-(2-hydroxyethyl)thiophene (1.28 g, 10.0 mmol), CSI (1.56 g, 11.0 mmol), and 3-amino-N-(3, 4-difluoro-phenyl)-4-methoxy-benzamide (1.95 g, 7.0 mmol) to give 0.360 g of pure carbamic acid, [[[5-[[(3,4-difluorophenyl)amino]carbonyl]-2-methoxyphenyl]amino] sulfonyl]-, 2-(3-thienyl)ethyl ester. $^1$HNMR (DMSO-d$_6$) δ 2.87–2.91 (m, 2H), 3.80 (s, 3H), 4.22–4.25 (m, 2H), 7.01–7.02 (d, 1H), 7.17–7.20 (m, 2H), 7.37–7.44 (m, 2H), 7.51–7.57 (m, 1H), 7.87–7.95 (m, 3H), 9.45 (s, 1H), 10.33 (s, 1H), 11.46 (s, 1H) ppm. Microanalysis: $C_{21}H_{19}F_2N_3O_6S_2$; calculated: C=49.31; H=3.74; N=8.21. found: C=48.91; H=3.76; N=8.09. MS: M$^+$+1=512.2 Da.

Example 12

Carbamic Acid, [[[5-(5,6-difluoro-IH-indol-2-yl)-2-methoxyphenyl]-amino]sulfonyl]-octyl ester The title compound was synthesized in the same manner as Example 1 using n-octanol (1.30 g, 10.0 mmol), CSI (1.56 g, 11.0 mmol), and 5-(5,6-difluoro-1H-indol-2-yl)-2-methoxy-phenylamine (2.33 g, 8.5 mmol) to give 0.935 g of pure carbamic acid, [[[5-(5,6-difluoro-1-H-indol-2-yl)-2-methoxyphenyl]amino]sulfonyl]-octyl ester. $^1$HNMR (DMSO-d$_6$) δ 0.77–0.81 (m, 3H), 1.14–1.25 (m, 10H), 1.47–1.55 (m, 2H), 3.78 (s, 3H), 4.00–4.04 (m, 2H), 6.72 (s, 1H), 7.12–7.14 (d, 1H), 7.25–7.30 (m, 1H), 7.74–7.46 (m, 1H), 7.61–7.67 (m, 2H), 9.27 (s, 1H), 11.38 (s, 1H), 11.62 (s, 1H) ppm. Microanalysis: $C_{24}H_{29}F_2N_3O_5S$; calculated: C=56.57; H=5.74; N=8.25. found: C=56.17; H=5.56; N=8.22. MS: M$^+$+1=510.3 Da.

Example 13

Carbamic Acid, [[[5-(5,6-difluoro-IH-indol-2-yl)-2-methoxyphenyl]amino]-sulfonyl]methyl-, 3 (phenylmethoxy)propyl ester To carbamic acid, [[[5-(5,6-difluoro-1H-indol-2-yl)-2-methoxyphenyl]-amino]sulfonyl]-3-(phenylmethoxy)propyl ester (0.70 g, 1.28 mmol) in THF (12 mL) was added sequentially, DBU (0.198 g, 1.3 mmol), and then methyl iodide (0.185 g, 1.3 mmol). The mixture stirred overnight at room temperature. The solution was diluted with methylene chloride (75 mL) and washed with water (75 mL). The organic phase dried over magnesium sulfate and then evaporated in vacuo to give the crude compound. This was purified by flash chromatography over silica gel (9:1, methylene chloride:ethyl acetate). The appropriate factions were combined and evaporated in vacuo to give 0.380 g of pure carbamic acid, [[[5-(5,6-difluoro-IH-indol-2-yl)-2-methoxyphenyl]amino]sulfonyl]methyl-, 3-(phenylmethoxy)propyl ester. $^1$HNMR (DMSO-d$_6$) δ 1.78–1.87 (m, 2H), 2.97 (s, 3H), 3.38–3.48 (m, 2H), 3.76 (s, 3H), 4.15–4.18 (m, 2H), 4.36 (s, 2H), 6.75 (s, 1H), 7.12–7.14 (d, 1H), 7.20–7.35 (m, 6H), 7.42–7.47 (m, 1H), 7.68–7.75 (m, 2H), 9.69 (s, 1H), 11.67 (s, 1H) ppm. Microanalysis: $C_{27}H_{27}F_2N_3O_6S$; calculated: C=57.95; H=4.86; N=7.53. found: C=57.99; H=4.94; N=7.33. MS: M$^+$+1=560.3 Da.

Example 14

Carbamic Acid, [[(5-(5,6-difluoro-IH-indol-2-yl)-2-methoxyphenyl]amino]-sulfonyl]-(phenylmethyl), 3-(phenylmethoxy)propyl ester The title compound was synthesized in the same manner as Example 13 using carbamic acid, [[[5-(5,6-difluoro-1H-indol-2-yl)-2-methoxyphenyl]amino]sulfonyl]-3-(phenylmethoxy)propyl ester (0.640 g, 1.17 mmol), benzyl bromide (0.205 g, 1.2 mmol), and DBU (0.183 g, 1.2 mmol) to give 0.215 g of pure carbamic acid, [[[5-(5,6-difluoro-IH-indol-2-yl)-2-methoxyphenyl]amino]sulfonyl] phenylmethyl)-, 3-(phenylmethoxy)propyl ester. $^1$HNMR (DMSO-d$_6$) δ 1.81–1.85 (m, 2H), 3.35–3.39 (m, 2H), 3.71 (s, 3H), 4.19–4.22 (m, 2H), 4.33 (s, 2H), 4.60 (s, 2H), 6.74 (s, 1H), 7.06–7.33 (m, 12H), 7.42–7.47 (m, 1H), 7.67–7.71 (m, 2H), 9.75 (s, 1H), 11.66 (s, 1H) ppm. Microanalysis: $C_{33}H_{31}F_2N_3O_6S$; calculated: C=62.35; H=4.92; N=6.61. found: C=62.26; H=5.00; N=6.27. MS: M$^+$+1=636.3 Da.

Example 15

Carbamic Acid, [[[5-(5,6-difluoro-IH-indol-2-yl)-2-methoxyphenyl]amino]sulfonyl]-2-(dimethylamino) ethyl ester, Monohydrochloride The title compound was synthesized in the same manner as Example 1 using 2-dimethylaminoethanol (0.802 g, 9.0 mmol), CSI (1.27 g, 9.0 mmol), and 5-(5,6-difluoro-1H-indol-2-yl)-2-methoxy-phenylamine (1.91 g, 7.0 mmol) to give 0.395 g of pure carbamic acid, [[[5-(5,6-difluoro-IH-indol-2-yl)-2-methoxyphenyl]amino]sulfonyl]-2-(dimethylamino)ethyl ester, monohydrochloride. $^1$HNMR DMSO-d$_6$) δ 2.71 (s, 6H), 3.20–3.40 (m, 2H), 3.80 (s, 3H), 420–4.35 (br. s, 2H), 6.66 (s, 1H), 7.08–7.10 (d, 1H), 7.26–7.30 (m, 1H), 7.44–7.52 (m, 2H), 7.77 (s, 1H), 11.63 (s, 1H) ppm. Microanalysis: $C_{20}H_{22}F_2N_4O_5S.0.25HCl.0.25 H_2O$; calculated: C=48.45; H=4.78; N=11.30. found: C=48.30; H=4.65; N=11.08. MS: M$^+$+1=469.3 Da.

Example 16

Acetic Acid, [[[[[5-(5,6-difluoro-IH-indol-2-yl)-2-methoxyphenyl]amino]-sulfonyl]amino]carbonyl] oxy]-, phenylmethyl ester The title compound was synthesized in the same manner as Example 1 using benzyl-2-hydroxyacetate (1.50 g, 9.0 mmol), CSI (1.27 g, 9.0 mmol), and 5(5,6-difluoro-1H-indol-2-yl)-2-methoxy-phenylamine (1.91 g, 7.0 mmol) to give 1.2 g of pure acetic acid, [[[[[5-(5,6-difluoro-1H-indol-2-yl)-2-methoxyphenyl]-amino]sulfonyl]amino]carbonyl]oxy]-, phenylmethyl ester. $^1$HNMR (DMSO-$d_6$) δ 3.75 (s, 3H), 4.77 (s, 2H), 5.16 (s, 2H), 6.76 (s, 1H), 7.12–7.14 (m, 1H), 7.26–7.33 (m, 6H), 7.42–7.47 (m, 1H), 7.64–7.7 (m, 2H), 9.51 (s, 1H), 11.61 (s, 1H), 11.77 (s, 1H) ppm. Microanalysis: $C_{25}H_{21}F_2N_3O_7S$; calculated: C=55.04; H=3.88; N=7.70. found: C=54.73; H=3.82; N=7.55. MS: M$^+$+1=546.2 Da.

Example 17

Benzamide, 3-[[[[[(3,5-dichlorophenyl)amino]-carbonyl]amino]sulfonyl]-amino]-N-(3,4-difluorophenyl)-4-methoxy The title compound was synthesized in the same manner as Example 1 using 3,5-dichloroaniline (1.0 g, 6.2 mmol), CSI (0.64 mL, 4.4 mmol), and 3-amino-N-(3,4-difluoro-phenyl)-4-methoxy-benzamide (1.24 g, 7.0 mmol) to give 0.05 g of pure benzamide, 3-[[[[[(3,5-dichlorophenyl)amino]-carbonyl]amino]sulfonyl]amino]-N-(3,4-difluorophenyl)-4-methoxy-. Microanalysis: $C_{21}H_{16}Cl_2F_2N_4O_5S$; calculated: C=46.25; H=2.96; N=10.27; found: C=46.30; H=3.32; N=9.93. MS: M$^+$+1=544.9 Da.

Example 18

Benzamide, N-(3,4-difluorophenyl)-4-methoxy-3-[[[[(phenylamino)carbonyl]-amino]sulfonyl]amino]

The title compound was synthesized in the same manner as Example 1 using aniline (0.59 g, 6.4 mmol), CSI (0.67 mL, 7.7 mmol), and 3-amino-N-(3,4-difluoro-phenyl)-4-methoxy-benzamide (1.19 g, 4.3 mmol) to give 0.17 g of pure benzamide, N-(3,4-difluorophenyl)-4-methoxy-3-[[[[(phenylamino)carbonyl]amino]sulfonyl]amino]-. Microanalysis: $C_{21}H_{18}F_2N_4O_5S$; calculated: C=52.94; H=3.81; N=11.76. found: C=52.70; H=4.04; N=11.51. MS: M$^+$+1=477 Da.

Example 19

Carbamic Acid, [[[5-[[(3,4-difluorophenyl)amino] carbonyl]-2-methoxyphenyl]amino]sulfonyl]-, Ethyl Ester The title compound was synthesized in the same manner as Example 1 using ethanol (0.52 g, 11.3 mmol), CSI (1.08 mL, 12.4 mmol), and 3-amino-N-(3,4-difluoro-phenyl)-4-methoxy-benzamide (1.1 g, 4.0 mmol) to give 0.65 g of pure carbamic acid, [[[5-[[(3,4-difluorophenyl)amino]carbonyl]-2-methoxyphenyl]amino]sulfonyl]-, ethyl ester. Microanalysis: $C_{17}H_{17}F_2N_3O_6S$; calculated: C=47.55; H=3.99; N=9.79. found: C=47.66; H=3.88; N=9.42. MS: M$^+$+1=430 Da.

Example 20

Benzamide, N-(3,4-difluorophenyl)-4-methoxy-3-[[[[[(4-methoxyphenyl)-amino]sulfonyl]amino] carbonyl]amino]

3-Amino-N-(3,4-difluoro-phenyl)-4-methoxy-benzamide (3.0 g, 10.8 mmol) was dissolved in 200 mL dichloromethane and added dropwise to a solution of CSI (1.15 mL, 12.9 mmol) in 50 mL of dichloromethane at 0° C. The resulting white suspension was stirred for 1 hour and then filtered to give 2.94 g of a chlorosulfonyl urea intermediate. This intermediate (1.4 g, 3.5 mmol) was added in portions to a solution of p-anisidine (0.43 g, 3.5 mmol) in 50 mL acetone with triethylamine (1.94 mL, 13.9 mmol). The resulting mixture was stirred for 16 hours at room temperature. The reaction mixture was concentrated in vacuo, and the residue was partitioned between ethyl acetate and 1 M HCl. The ethyl acetate layer was dried over magnesium sulfate, filtered, and concentrated to give a pale pink oily solid. Recrystallization from dichloromethane gave 0.55 g of pure benzamide, N-(3,4-difluorophenyl)-4-methoxy-3-[[[[[(4-methoxyphenyl)amino]-sulfonyl]amino]carbonyl]amino]-. Microanalysis: $C_{22}H_{20}F_2N_4O_6S$; calculated: C=52.17; H=3.98; N=11.06. found: C=52.20; H=4.06; N=10.98. MS: M$^+$+1=507 Da.

Example 21

Carbamic Acid, [[[5-(5,6-difluoro-IH-indol-2-yl)-2-methoxyphenyl]amino]-sulfonyl]-, Butyl Ester To a cold solution of chlorosulfonylisocyanate (3.1 g, 0.022 mol) in dichloromethane (20 mL) was added dropwise a solution of n-butanol (1.5 g, 0.020 mol) in dichloromethane (5 mL). The solution gradually warmed to room temperature and was stirred overnight. The solvent was concentrated in vacuo leaving a viscous liquid. The crude product was triturated with hexane/ethyl acetate (4:1) and concentrated to give the sulfamoyl chloride intermediate as a white solid. The solid was suspended in hexane and collected by filtration. Yield: 3.4 g, (87%) of chlorosulfonyl-carbamic acid, n-butyl ester, which was used without further characterization.

A solution of the chlorosulfonyl carbamic acid, n-butyl ester (3.4 g, 0.018 mol) in benzene (25 mL) was added dropwise at room temperature to a stirred solution of triethylamine (4.5 g, 0.044 mol) in benzene (25 mL). The reaction mixture was stirred overnight, filtered, and the filtrate was concentrated in vacuo to give a viscous liquid. A portion of the liquid obtained (0.5 g, 1.78 mmol) was diluted with benzene (50 mL) and treated with 5-(5,6-difluoro-1H-indol-2-yl)-2-methoxy-phenylamine (0.48 g, 1.78 mmol) in one portion. The reaction mixture was stirred at room temperature overnight, at which time it was diluted with aqueous HCl (25 mL) and ethyl acetate (50 mL). The organic phase was separated and washed with brine, dried (MgSO$_4$), and concentrated. The resulting residue was recrystallization from hexane/ethyl acetate to give 0.12 g (15%) of carbamic acid, [[[5-(5,6-difluoro-1H-indol-2-yl)-2-methoxyphenyl)-amino]sulfonyl]-, butyl ester. Mp 193–194° C.; $^1$HNMR (CDCl$_3$/DMSO-$d_6$) δ 11.1 (s, 1H), 9.3 ((s, 1H), 7.9 (s, 1H), 7.7–7.6 (m, 3H), 7.3 (m, 1H), 7.1 (m, 1H), 6.9 (d, 1H), 3.9 (s, 3H), 3.8 (d, 2H), 1.8 (m, 1H), 0.8 (m, 6H) ppm. Microanalysis: $C_{19}H_{22}F_2N_3O_6S$; calculated: C=49.78; H=4.84; N=9.17. found: C=49.88; H=4.53; N=9.16. MS:M$^+$+1=457 Da.

Example 22

Carbamic Acid, [[[5-(5,6-difluoro-IH-indol-2-yl)-2-methoxyphenyl]amino]-sulfonyl]-, 2-methylpropyl ester The title compound was synthesized in the same manner as Example 1 using isobutanol (1.5 g 0.020 mol) to give 0.15 g (18%) of pure carbamic acid, [[[5-(5,6-difluoro-1H-indol-2-yl)-2-methoxyphenyl]amino]sulfonyl]-, 2-methylpropyl ester, which was isolated as a cream colored solid. Mp 187–189° C.; $^1$HNMR (CDCl$_3$/DMSO-d$_6$) δ 11.0 (s, 1H), 10.4 (s, 1H), 7.7 (s, 1H), 7.6 (s, 1H), 7.4 (d, 1H), 7.3 (m, 1H), 7.1, (m, 1H), 6.9 (d, 1H), 6.6 (s, 1H), 3.8 (s, 3H), 3.78 (d, 2H), 1.8, (m, 1H), 0.7 (d, 6H) ppm. Microanalysis: C$_{20}$H$_{21}$F$_2$N$_3$O$_5$S; calculated: C=52.97; H=4.67; N=9.27. found: C=52.64; H=4.57; N=9.10. MS: M$^+$+1=453 Da.

Example 23

Carbamic Acid, [[(5-[[(3,4-difluorophenyl)amino] carbonyl]-2-methoxyphenyl]amino]sulfonyl]-, 2-methylpropyl ester The title compound was prepared by replacing 5-(5,6-difluoro-1H-indol-2-yl)-2-methoxy-phenylamine with 3-amino-N-(2,4-difluorophenyl)-4-methoxy-benzamide (0.49 g, 1.78 mmol) in the procedure used in Example 22 to give 0.17 g (21%) of pure carbamic acid, [[(5-[[(3,4-difluorophenyl)amino]carbonyl]-2-methoxyphenyl]amino] sulfonyl]-, 2-methylpropyl ester as a white powder. Mp 188–190° C.; $^1$HNMR (CDCl$_3$/DMSO-d$_6$) δ 10.9 (s, 1H), 10.3 (s, 1H), 7.7 (s, 1H), 7.6 (s, 1H), 7.4 (d, 1H), 7.3 (m, 1H), 7.1 (m, 1H), 6.9 (d, 1H), 6.6 (s, 1H), 4.1 (t, 2H), 3.9 (s, 3H), 1.5 (m, 2H), 1.2 (m, 2H), 0.8 (t, 3H) ppm. Microanalysis: C$_{20}$H$_{21}$F$_2$N$_3$O$_5$S.0.38H$_2$O; calculated: C=52.19; H=4.76; N=9.13. found: C=52.18; H=4.80; N=8.96. MS: M$^+$+1=457 Da.

Example 24

Urea, N-(3,5-dichlorophenyl)-]-N'-[[[5-(5,6-difluoro-1H-indol-2-yl)-2-methoxyphenyl]amino] sulfonyl]

Urea, N-(3,5-dichlorophenyl)-]-N'-[[[5-(5,6-difluoro-1H-indol-2-yl)-2-methoxyphenyl]amino]sulfonyl] was synthesized in the same manner as Example 1 using 3,5-dichloroaniline (2.0 g, 12.3 mmol), CSI (1.28 mL, 14.8 mmol), and 5-(5,6-difluoro-1H-indol-2-yl)-2-methoxy-phenylamine (1.0 g, 3.3 mmol); Microanalysis: C$_{22}$H$_{16}$Cl$_2$F$_2$N$_4$O$_4$S.2.0H$_2$O; calculated: C=45.77; H=3.49; N=9.70. found: C=45.79; H=3.08; N=9.68. MS: M$^+$=541 Da.

Example 25

Carbamic Acid, [[[5-(5,6-difluoro-1H-indol-2-yl)-2-methoxyphenyl]amino]-sulfonyl]-, ethyl ester Carbamic acid, [[[5-(5,6-difluoro-1H-indol-2-yl)-2-methoxyphenyl]amino]sulfonyl]-, ethyl ester was synthesized in the same manner as Example 1 using 5-(5,6-difluoro-1H-indol-2-yl)-2-methoxy-phenylamine (0.5 g, 1.8 mmol) and Et$_3$NSO$_2$NCO$_2$Et (0.46 g, 1.8 mmol); Microanalysis: C$_{18}$H$_{17}$F$_2$N$_3$O$_5$S.C$_4$H$_8$O$_2$; calculated: C=51.46; H=4.91; N=8.18; found: C=51.86; H=4.57; N=8.58. MS: M$^+$+1=426.1 Da.

Example 26

Carbamic Acid, [[[5-(1H-indol-2-yl)-2-methoxyphenyl]amino]sulfonyl]-, Ethyl Ester Carbamic acid, [[[5-(1H-indol-2-yl)-2-methoxyphenyl] amino]sulfonyl]-, ethyl ester was synthesized in the same manner as Example 1 using 5-(1H-indol-2-yl)-2-methoxy-phenylamine (0.87 g, 3.64 mmol) and Et$_3$NSO$_2$NCO$_2$Et (0.92 g, 3.64 mmol); Microanalysis: C$_{18}$H$_{19}$N$_3$O$_5$S; calculated: C=55.52; H=4.92; N=10.79. found: C=55.30; H=5.04; N=10.39. MS: M$^+$+1=390.1 Da.

Example 27

Urea, N-(4-chlor phenyl)-N'-[[[5-(5,6-difluoro-1H-indol-2-yl)-2-methoxyphenyl]amino]sulfonyl]

Urea, N-(4-chlorophenyl)-N'-[[[5-(5,6-difluoro-1H-indol-2-yl)-2-methoxyphenyl]amino]sulfonyl] was synthesized in the same manner as Example 1 using 5-(5,6-difluoro-1H-indol-2-yl)-2-methoxy-phenylamine (0.41 g, 1.5 mmol) and (4-chlorophenyl)NHCONHSO$_2$Cl (0.4 g, 1.5 mmol); Microanalysis: C$_{22}$H$_{17}$Cl$_2$F$_2$N$_4$O$_4$S.0.5 H$_2$O; calculated: C=52.19; H=4.76; N=9.13. found: C=52.18; H=4.80; N=8.96. MS: M$^+$+1=507 Da.

Example 28

Urea, N-[[[5-(5,6-difluoro-1H-indol-2-yl)-2-methoxyphenyl]amino]sulfonyl]-N'-(4-methylphenyl)

Urea, N-[[[5-(5,6-difluoro-1H-indol-2-yl)-2-methoxyphenyl]amino]-sulfonyl]-N'-(4-methylphenyl) was synthesized in the same manner as Example 1 using 5-(5,6-difluoro-1H-indol-2-yl)-2-methoxy-phenylamine (0.33 g, 1.2 mmol) and (4-methylphenyl)NHCONHSO$_2$Cl (0.3 g, 1.2 mmol); Microanalysis: C$_{23}$H$_{20}$F$_2$N$_4$O$_4$S.1.75 H$_2$O; calculated: C=53.33; H=4.57; N=10.82. found: C=53.41; H=4.16; N=10.42. MS: M$^+$+1=487 Da.

Example 29

Carbamic Acid, [[[5-(5,6-difluoro-1H-indol-2-yl)-2-methoxyphenyl]amino]-sulfonyl]-methyl ester Carbamic acid, [[[5-(5,6-difluoro-1H-indol-2-yl)-2-methoxyphenyl]-amino]sulfonyl]-methyl ester was synthesized in the same manner as Example 1 using 5-(5,6-difluoro-1H-indol-2-yl)-2-methoxy-phenylamine and Et$_3$NSO$_2$NCO$_2$Me; Microanalysis: C$_{20}$H$_{21}$F$_2$N$_3$O$_5$S.0.38 H$_2$O; calculated: C=52.19; H=4.76; N=9.13. found: C=52.18; H=4.80; N=8.96. MS: M$^+$+1=457 Da.

Example 30

Carbamic Acid, [[[5-(5,6-difluoro-1H-indo-2-yl)2-methoxyphenyl]amino]-sulfonyl]-heptyl ester The title compound was synthesized as in Example 1 using heptyl alcohol (1.3 mL, 8.9 mmol), CSI (0.85 mL, 9.8 mmol), and 5-(5,6-difluoro-1H-indol-2-yl)-2-methoxy-phenylamine (2.4 g, 8.9 mmol) to give 2.9 g of carbamic acid, [[[5-(5,6-difluoro-1H-indol-2-yl)-2-methoxyphenyl] amino]sulfonyl]-heptyl ester. Microanalysis: C$_{23}$H$_{27}$F$_2$N$_3$O$_5$S; calculated: C=55.75; H=5.49; N=8.48; found: C=55.64; H=5.61; N=8.41. MS: M$^+$+1=496 Da. Mp 178–180° C. $^1$HNMR (400 MHz, DMSO-d$_6$) δ 11.63 (s, 1H), 11.38 (s, 1H), 9.27 (s, 1H), 7.67 (d, J=1.9 Hz, 1H), 7.62 (d, J=8.7 Hz, 1H), 7.49–7.44 (m, 1H), 7.30–7.26 (m, 1H), 7.13 (d, J=8.4 Hz, 1H), 6.72 (s, 1H), 4.02 (t, J=6.5 Hz, 2H), 3.78 (s, 3H), 1.17–1.13 (m, 10H), 0.78 (t, J=6.5 Hz, 3H).

Example 31

Carbamic Acid, [[[5,6-difluoro-1H-indol-2-yl)-2-methoxyphenyl]amino]-sulfonyl]-pentyl ester The title compound was synthesized as in Example 1 using pentyl alcohol (0.97 mL, 8.9 mmol), CSI (0.85 mL, 9.8 mmol), and 5-(5,6-difluoro-1H-indol-2-yl)-2-methoxy-phenylamine (2.4 g, 8.9 mmol), to give 2.9 g of carbamic acid, [[[5-(5,6-difluoro-IH-indol-2-yl)-2-methoxyphenyl]amino]sulfonyl)-pentyl ester. Microanalysis: $C_{21}H_{23}F_2N_3O_5S$; calculated: C=53.95; H=4.96; N=8.99; found: C=53.86; H=5.06; N=8.95. MS: $M^++1$=468 Da. Mp 182–184° C. $^1$HNMR (400 MHz, DMSO-$d_6$) δ 11.63 (s, 1H), 11.38 (s, 1H), 9.27 (s, 1H), 7.68 (s, 1H), 7.62 (d, J=8.4 Hz, 1H), 7.49–7.44 (m, 1H), 7.30–7.26 (m, 1H), 7.14 (d, J=8.7 Hz, 1H), 6.72 (s, 1H), 4.03 (t, J=6.8 Hz, 2H), 3.78 (s, 3H), 1.20–1.13 (m, 6H), 0.78 (t, J=6.5 Hz, 3H).

Example 32

Carbamic Acid, [[[5-(5,6-difluoro-IH-indol-2-yl)-2-methoxyphenyl]amino]sulfonyl]-(2E)-3-phenyl-2-propenyl ester The title compound was synthesized as in Example 1 using cinnamyl alcohol (0.99 g, 7.3 mmol), CSI (0.42 mL, 4.9 mmol), and 5-(5,6-difluoro-1H-indol-2-yl)-2-methoxyphenylamine (1.0 g, 3.6 mmol) to give 0.51 g of carbamic acid, [[[5-(5,6-difluoro-IH-indol-2-yl)-2-methoxyphenyl]amino]sulfonyl]-(2E)-3-phenyl-2-propenyl ester. Microanalysis: $C_{25}H_{21}F_2N_3O_5S$; calculated: C=58.47; H=4.12; N=8.18. found: C=58.59; H=4.09; N=8.20. MS: $M^++1$=514 Da. Mp 149–152° C. $^1$HNMR (400 MHz, DMSO-$d_6$) δ 11.66 (s, 1H), 11.51 (s, 1H), 9.44 (s, 1H), 7.71 (s, 1H), 7.66–7.64 (m, 1H), 7.46–7.13 (m, 8H), 6.75–6.65 (m, 2H), 6.37–6.30 (m, 1H), 4.77 (d, J=6.1 Hz, 2H), 3.78 (s, 3H).

Example 33

Carbamic Acid, [[[5-[[(3,4-difluorophenyl)amino]carbonyl]-2-methoxyphenyl]amino]sulfonyl]-, (2E)-3-phenyl-2-propenyl ester The title compound was synthesized as in Example 1 using cinnamyl alcohol (0.99 g, 7.3 mmol), CSI (0.42 mL, 4.9 mmol), and 3-amino-N-(3,4-difluorophenyl)-4-methoxy-benzamide (1.0 g, 3.6 mmol) to give 0.55 g of carbamic acid, [[[5-[[(3,4-difluorophenyl)amino]carbonyl]-2-methoxyphenyl]amino]sulfonyl]-, (2E)-3-phenyl-2-propenyl ester. Microanalysis: $C_{24}H_{21}F_2N_3O_6S.0.18 C_6H_{16}NCl$; calculated: C=55.55; H=4.44; N=8.21; found: C=55.32; H=4.16; N=8.30. MS: $M^+-1$=516 Da. Mp 159–163° C. $^1$HMR (400 MHz, DMSO) δ 11.49 (s, 1H), 10.34 (s, 1H), 9.53 (s, 1H), 7.93–7.87 (m, 3H), 7.54–7.16 (m, 8H), 6.70–6.66 (m, 1H), 6.38–6.31 (m, 1H), 4.76–4.75 (d, J=5.8 Hz, 2H), 3.82 (s, 3H).

Example 34

Carbamic Acid, [[[5-(5,6-difluoro-IH-indol-2-yl)-2-methoxyphenyl]amino]-sulfonyl]-2(1-methylethoxy) ethyl Ester The title compound was synthesized as in Example 1 using 2-isopropoxyethanol (0.47 mL, 4.0 mmol), CSI (0.42 mL, 4.9 mmol), and 5-(5,6-difluoro-1H-indol-2-yl)-2-methoxy-phenylamine (1.0 g, 3.6 mmol) to give 0.67 g of carbamic acid, [[[5-(5,6-difluoro-IH-indol-2-yl)-2-methoxyphenyl]-amino]sulfonyl]-2-(1-methylethoxy)ethyl ester. Microanalysis: $C_{21}H_{23}F_2N_3O_6S.0.3 C_6H_{16}NCl.0.41H_2O$; calculated: C=51.46; H=5.42; N=8.69. found: C=51.45; H=5.18; N=8.85. MS: $M^++1$=484 Da. Mp 158–163° C. $^1$HNMR (400 MHz, DMSO-$d_6$) δ 11.64 (s, 1H), 11.53 (s, 1H), 9.27 (s, 1H), 7.71 (s,1H), 7.62 (d, J=7.7 Hz, 1H), 7.50–7.46 (m, 1H), 7.32–7.28 (m, 1H), 7.14 (d, J=8.4 Hz, 1H), 6.74 (s, 1H), 4.13 (s, 2H), 3.80 (s, 3H), 3.52–3.47 (m, 3H), 1.00 (d, J=6.0 Hz, 6H).

Example 35

Carbamic Acid, [[[5-[[(3,4-difluorophenyl)amino]carbonyl]-2-methoxyphenyl]amino]sulfonyl]-, 2-(1-methylethoxy)ethyl ester The title compound was synthesized as in Example 1 using 2-isopropoxyethanol (0.47 mL, 4.0 mmol), CSI (0.42 mL, 4.9 mmol), and 3-amino-N-(3,4-difluoro-phenyl)-4-methoxy-benzamide (1.0 g, 3.6 mmol) to give 0.76 g of carbamic acid, [[[5-[[(3,4-difluorophenyl)amino]carbonyl]-2-methoxyphenyl]amino]sulfonyl]-, 2-(1-methylethoxy) ethyl ester. Microanalysis: $C_{20}H_{23}F_2N_3O_7S$; calculated: C=49.28; H=4.76; N=8.62; found: C=49.08; H=4.66; N=8.43. MS: $M^++1$=488 Da. $^1$HNMR (400 M DMSO-$d_6$)δ 11.50 (s, 1H), 10.33 (s, 1H), 9.42 (s, 1H), 7.95–7.86 (m, 3H), 7.54–7.52 (m, 1H), 7.45–7.38 (m, 1H), 7.19 (d, J=8.7 Hz, 1H), 4.16–4.14 (m, 2H), 3.84 (s, 3H), 3.56–3.50 (m, 3H), 1.03 (d, J=6.0 Hz, 6H).

Example 36

Carbamic Acid, [[[5-(5,6-difluoro-IH-indol-2-yl)-methoxyphenyl]amino]-sulfonyl]-, Phenylmethyl ester The title compound was synthesized as in Example 1 using benzyl alcohol (0.44 mL, 4.0 mmol), CSI (0.42 mL, 4.9 mmol), and 5-(5,6-difluoro-1H-indol-2-yl)-2-methoxy-phenylamine (1.0 g, 3.6 mmol) to give 0.56 g of carbamic acid, [[[5-(5,6-difluoro-IH-indol-2-yl)-2-methoxyphenyl]amino]sulfonyl]-, phenylmethyl ester. Microanalysis: $C_{23}H_{19}F_2N_3O_5S$; calculated: C=56.67; H=3.93; N=8.62. found: C=56.29; H=3.76; N=8.41. MS: $M^++1$=488 Da. Mp 177–180° C. $^1$HNMR (400 MHz, DMSO-$d_6$) δ 11.65 (s, 1H), 11.54 (s, 1H), 9.41 (s, 1H), 7.70 (s, 1H), 7.65 (d, J=8.7 Hz, 1H), 7.49–7.44 (m, 1H), 7.32–7.27 (m, 6H), 7.14 (d, J=8.4 Hz, 1H), 6.72 (s, 1H), 5.15 (s, 2H), 3.73 (s, 3H).

Example 37

Sulfamide, N-[5-(5,6-diflouo-IH-indo-2-yl)-2-methoxyphenyl]-N'-methyl

Methyl sulfamic acid (2.0 g, 18.0 mmol) was suspended in benzene, and phosphorous pentachloride (3.7 g, 18.0 mmol) was added The mixture was refluxed for 3 hours. The supernatant was decanted into a separate flask, leaving any solid behind. The benzene was removed by distillation, and the remaining oil, methyl sulfamyl chloride, was stored under nitrogen. Methyl sulfamyl chloride (0.80 g, 6.2 mmol) was dissolved in 50 mL of methylene chloride, and 5-(5,6-difluoro-1H-indol-2-yl)-2-methoxy-phenylamine (1.0 g, 3.6 mmol) and triethylamine (1.0 mL, 7.2 mmol) were added. The solution was stirred overnight The resulting mixture was washed with water (2×50 mL), and the organic phase was dried over magnesium sulfate. The solvents were evaporated under reduced pressure to give a foam. The foam was redissolved in a small amount of fresh methylene chloride and treated with 1N hydrochloric acid. (20 mL). Vigorous shaking produced a precipitate, which was collected via filtration. The resulting powder was triturated sequentially with water, methylene chloride, and ether. The triturated solid was dried under vacuum to give 0.26 g of sulfamide, N-[5-(5,6-difluoro-IH-indol-2-yl)-2-methoxyphenyl]-N'-methyl-. Microanalysis: $C_{15}H_{15}F_2N_3O_4S.0.15 CH_2Cl_2.0.08 C_6H_{16}NCl$; calculated: C=51.07; H=4.27; N=11.03. found: C=51.13; H=4.26; N=10.83. MS: $M^++1$=368 Da. Mp 196–200° C. $^1$HNMR (400 Mz, DMSO-$d_6$) δ 11.59 (s, 1H), 8.55 (s, 1H), 7.70 (s,1H), 7.55–7.45 (m, 1H), 7.32–7.28 (m, 1H), 7.18 (d, J=4.3 Hz, 1H), 7.15 (d, J=8.7 Hz, 1H), 6.73 (s, 1H), 3.84 (s, 3H), 2.53 (s, 3H).

Example 38

Benzamide, N-(3,4-difluorophenyl)-4-methoxy-3-[[(methylamino)-sulfonyl]amino]

The title compound was synthesized as in Example 37 using methyl sulfonyl chloride (0.8 g, 6.2 mmol) and 3-amino-N-(3,4-difluoro-phenyl)-4methoxy-benzamide (1.0 g, 3.6 mmol) to give 0.48 g of benzamide, N-(3,4-difluorophenyl)-4-methoxy-3-[[(methylamino) sulfonyl]amino]-. Microanalysis: $C_{15}H_{15}F_2N_3O_4S$. 0.04 $CH_2Cl_2$.0.91$H_2O$; calculated: C=46.18; H=4.35; N=10.74. found: C=46.18; H=4.36; N=10.64. MS: $M^++1$=372 Da. $^1$HNMR (400 MHz, DMSO-$d_6$) δ 10.26 (s, 1H), 8.60 (s, 1H), 7.93–7.88 (m, 2H), 7.74 (d, 8.4 Hz, 1H), 7.52–7.50 (m, 1H), 7.36 (q, J=9.4, 10.4 Hz, 1H), 7.13 (d, J=8.7 Hz, 2H), 3.88 (s, 3H), 2.49 (s, 3H).

Example 39

Carbamic Acid, [[[5-[[(3,4-difluorophenyl)amino]carbonyl]-2-methoxyphenyl]amino]sulfonyl]-, 3-(4-pyridinyl)propyl ester The title compound was synthesized as in Example 1 using 3-(4-pyridyl)-1-propanol (0.55 g, 4.0 mmol), CSI (0.42 mL, 4.9 mmol), and 3-amino-N-(3,4-difluoro-phenyl)-4-methoxy-benzamide (1.0 g, 3.6 mmol) to give 0.08 g of carbamic acid, [[[5-[[(3,4-difluorophenyl)amino]carbonyl]-2-methoxyphenyl]amino]sulfonyl]-, 3-(4-pyridinyl)propyl ester. Microanalysis: $C_{23}H_{22}F_2N_4O_6S$.0.08 $C_6H_{16}NCl$.0.48 $H_2O$; calculated: C=52.21; H=4.52; N=10.58. found: C=52.20; H=4.53; N=10.30. MS: $M^++1$=521 Da. Mp 160–164° C. $^1$HNMR (400 MHz, DMSO-$d_6$) δ 11.33 (s, 1H), 10.15 (s, 1H), 8.48 (s, 1H), 7.91–7.86 (m, 3H), 7.50–7.17 (m, 6H), 4.05 (t, J=6.5 Hz, 2H), 3.81 (s, 3H), 2.65 (t, J=7.2 Hz, 2H), 1.89 (t, J=6.5 Hz, 2H).

Example 40

Carbamic Acid, [[[5-(5,6-difluoro-IH-indol-2-yl)-2-methoxyphenyl]amino]-sulfonyl]-2-phenylethyl ester The title compound was synthesized as in Example 1 using phenethyl alcohol (0.48 mL, 4.0 mmol), CSI (0.42 mL, 4.9 mmol), and 5-(5,6-difluoro-1H-indol-2-yl)-2-methoxy-phenylamine (1.0 g, 3.6 mmol) to give 0.75 g of carbamic acid, [[[5-(5,6-difluoro-IH-indol-2-yl)-2-methoxyphenyl]amino]sulfonyl]-2-phenylethyl ester. Microanalysis: $C_{24}H_{21}F_2N_3O_5S$.0.1 $C_6H_{16}NCl$.0.17 $H_2O$; calculated: C=57.00; H=4.46; N=8.33. found: C=57.00; H=4.33; N=8.27. MS: $M^++1$=502 Da. Mp 180–182° C. $^1$HNMR (400 Mz, DMSO-$d_6$) δ 11.65 (s, 1H), 11.47 (s, 1H), 9.30 (s, 1H), 7.70 (s, 1H), 7.65 (d, J=8.4 Hz, 1H), 7.50–7.45 (m, 1H), 7.32–7.27 (m, 1H), 7.24–7.12 (m, 6H), 6.74 (s, 1H), 4.24 (t, J=7.0 Hz, 2H ), 3.74 (s, 3H), 2.85 (t, J=7.0 Hz, 2H).

Example 41

Carbamic Acid, [[[[5-[[(3,4-difluorophenyl)amino]carbonyl]-2-methoxyphenyl]amino]sulfonyl]-, 2-phenylethyl ester The title compound was synthesized as in Example 1 using phenethyl alcohol (0.48 mL, 4.0 mmol), CSI (0.42 mL, 4.9 mmol), and 3-amino-N-(3,4-difluoro-phenyl)-4-methoxy-benzamide (1.0 g, 3.6 mmol) to give 1.16 g of carbamic acid, [[[5-[[(3,4-difluorophenyl)amino]carbonyl]-2-methoxyphenyl]-amino]sulfonyl]-, 2-phenylethyl ester. Microanalysis: $C_{23}H_{21}F_2N_3O_6S$.0.2 $C_6H_{16}NCl$.0.14 $H_2O$; calculated: C=54.27; H=4.61; N=837. found: C=54.27; H=4.33; N=8.21. MS: $M^++1$=506 Da. Mp 173–177° C. 1HNMR (400 MHz, DMSO-$d_6$) δ 11.45 (s, 1H), 10.34 (s, 1H), 9.41 (s, 1H), 7.94–7.87 (m, 3H), 7.54–7.51 (m, 1H), 7.43–7.36 (q, J=9.2, 10.1 Hz, 1H), 7.26–7.16 (m, 6H), 4.24 (t, J=6.8 Hz, 2H), 3.78 (s, 3H), 2.86 (t, J=6.8 Hz, 2H).

Example 42

Carbamic Acid, [[[5-[[(3,4-difluorophenyl)amino]carbonyl]-2-methoxyphenyl]amino]sulfonyl]-, Phenylmethyl Ester The title compound was synthesized as in Example 1 using benzyl alcohol (0.44 mL, 4.0 mmol), CSI (0.42 mL, 4.9 mmol), and 3-amino-N-(3,4-difluorophenyl)-4-methoxy-benzamide (1.0 g, 3.6 mmol) to give 1.0 g of carbamic acid, [[[5-[[(3,4-difluorophenyl)amino]carbonyl]-2-methoxyphenyl]amino]sulfonyl]-, phenylmethyl ester. Microanalysis: $C_{22}H_{19}F_2N_3O_6S$; calculated: C=53.77; H=3.90; N=8.55. found: C=53.49; H=3.83; N=8.63. MS: $M^++1$=492 Da. Mp 173–176° C. $^1$HNMR (400 MHz, DMSO-$d_6$) δ 11.53 (s, 1H), 10.33 (s, 1H), 9.53 (s, 1H), 7.95–7.86 (m, 3H), 7.54–7.51 (m, 1H), 7.44–730 (m, 6H), 7.18 (d, J=8.7 Hz, 1H), 5.15 (s, 2H), 3.77 (s, 3H).

Example 43

Acetic Acid, [[[[[5-(5,6-difluoro-1H-indol-2-yl)-2-methoxyphenyl]amino]-sulfonyl]amino]carbonyl]oxy]-, Methyl ester The title compound was synthesized as in Example 1 using methyl glycolate (0.36 g, 4.0 mmol), CSI (0.42 mL, 4.9 mmol), and 5-(5,6-difluoro-1H-indol-2-yl)-2-methoxy-phenylamine (1.0 g, 3.6 mmol) to give 0.28 g of acetic acid, [[[[[5-(5,6-difluoro-1H-indol-2-yl)-2-methoxyphenyl]amino]-sulfonyl]amino]carbonyl]oxy]-, methyl ester. Microanalysis: $C_{19}H_{17}F_2N_3O_7S$.0.55 $C_4H_8O_2$.0.12 $H_2O$; calculated: C=48.95; H=3.96; N=8.07. found: C=48.95; H=3.92; N=8.07. MS: $M^++1$=470 Da. Mp 190–192° C. $^1$HNMR (400 MHz, DMSO-$d_6$) δ 11.76 (s, 1H), 11.62 (s, 1H), 9.49 (s, 1H), 7.70 (s, 1H), 7.66 (d, J=8.7 Hz, 1H), 7.50–7.45 (m, 1H), 7.32–7.27 (m, 1H), 7.15 (d, J=8.4 Hz, 1H), 6.77 (s, 1H), 4.72 (s, 2H), 3.79 (s, 3H), 3.65 (s, 3H).

Example 44

Acetic Acid, [[[[[5-[[(3,4-difluorophenyl)amino]carbonyl]-2-methoxyphenyl]-amino]sulfonyl]amino]carbonyl]oxy]-, Methyl ester The title compound was synthesized as in Example 1 using methyl glycolate (0.36 g, 4.0 mmol), CSI (0.42 mL 4.9 mmol), and 3-amino-N-(3,4-difluoro-phenyl)-4-methoxy-benzamide (1.0 g, 3.6 mmol) to give 0.55 g of acetic acid, [[[[[5-[[(3,4-difluorophenyl)amino]carbonyl]-2-methoxyphenyl]amino]sulfonyl]amino]carbonyl]oxy]-, methyl ester. Microanalysis: $C_{18}H_{17}F_2N_3O_8S$; calculated: C=45.67; H=3.62; N=8.88; found: C=45.43; H=3.46; N=8.95. MS: $M^++1$=474 Da. Mp 177–180° C. $^1$HNMR (400 MHz, DMSO-$d_6$) δ 11.76 (s, 1H), 10.31 (s, 1H), 9.58 (s, 1H), 7.94–7.86 (m, 3H), 7.53–7.51 (m, 1H), 7.40 (q, J=10.4, 9.2 Hz, 1H), 7.19 (d, J=8.7 Hz, 1H), 4.70 (s, 2H), 3.83 (s, 3H), 3.65 (s, 3H).

Example 45

Carbamic acid, [[[5-(5,6-difluoro-IH-indol-2-yl)-2-methoxyphenyl]amino]-sulfonyl]-3-hydroxypropyl ester Carbamic acid, [[[5-(5,6-difluoro-1H-indol-2-yl)-2-methoxyphenyl]-amino]sulfonyl]-3-(phenylmethoxy)propyl ester (0.25 g, 0.5 mmol) and a catalytic amount of 20% palladium on carbon were stirred together in methanol under an atmosphere of hydrogen. After 1.5 hours, the methanol mixture was filtered through Celite, and the filtrate was concentrated under reduced pressure to give a clear oil. The oil was triturated with diethyl ether, resulting in a precipitate of 0.11 g of carbamic acid, [[[5-(5,6-difluoro-IH-indol-2-yl-2-methoxyphenyl]amino]sulfonyl]-3-hydroxypropyl ester. Microanalysis: $C_{19}H_{19}F_2N_3O_6S$; calculated: C=50.11; H=4.21; N=9.23. found: C=49.71; H=4.26; N=8.90. MS: $M^++1=456$ Da. $^1$HNMR (400 MHz, DMSO-$d_6$) δ 11.64 (s, 1H), 11.36 (s, 1H), 9.32 (s, 1H), 7.69 (s, 1H), 7.65 (d, J=8.7 Hz, 1H), 7.50–7.46 (m, 1H), 7.32–7.27 (m, 1H), 7.15 (d, J=8.4 Hz, 1H), 6.73 (s, 1H); 4.52 (s, 1H), 4.13 (t, J=6.5 Hz, 2H), 3.79 (s, 3H), 3.43 (t, J=6.0 Hz, 2H), 1.73–1.67(m, 2H).

Example 46

Carbamic Acid, [[[5-[[(3,4-difluorophenyl)amino]carbonyl]-2-methoxyphenyl]amino]sulfonyl]-, 3-hydroxypropyl ester The title compound was synthesized as in Example 45 using carbamic acid, [[[5-[[(3,4-difluorophenyl)amino]carbonyl]-2-methoxyphenyl]amino]sulfonyl]-, 3-(phenylmethoxy)propyl ester (0.25 g, 0.40 mmol) to give 0.18 g of carbamic acid, [[[5-[[(3,4-difluorophenyl)amino]carbonyl]-2-methoxyphenyl]-amino]sulfonyl]-, 3-hydroxypropyl ester. Microanalysis: $C_{18}H_{19}F_2N_3O_7S$; calculated: C=47.06; H=4.17; N=9.15. found: C=46.79; H=4.16; N=9.04. MS: $M^++1=460$ Da. Mp 178–179° C. $^1$HNMR (400 MHz, DMSO-$d_6$) δ 11.34 (s, 1H), 10.32 (s, 1H), 9.42 (s, 1H), 7.94–7.85 (m, 3H), 7.52–7.51 (m, 1H), 7.40 (q, J=9.2, 9.4 Hz, 1H), 7.18 (d, J=8.7 Hz, 1H), 4.51 (s, 1H), 4.11 (t, J=6.5 Hz, 2H), 3.83 (s, 3H), 3.42 (t, J=6.0 Hz, 2H), 1.72–1.66 (m, 2H).

Example 47

Carbamic Acid, [[[5-(5,6-difluoro-IH-indol-2-yl)-2-methoxyphenyl]-amino]sulfonyl]-, 2-ethoxyethyl ester The title compound was synthesized as in Example 1 using 2-ethoxyethanol (0.40 mL, 4.0 mmol), CSI (0.42 mL, 4.9 mmol), and 5-(5,6-difluoro-1H-indol-2-yl)-2-methoxy-phenylamine (1.0 g, 3.6 mmol) to give 0.43 g of carbamic acid, [[[5-(5,6-difluoro-IH-indol-2-yl)-2-methoxyphenyl]amino]sulfonyl]-, 2-ethoxyethyl ester. Microanalysis: $C_{20}H_{21}F_2N_3O_6S$; calculated: C=51.17; H=4.51; N=8.95. found: C=51.18; H=4.55; N=8.81. MS: $M^++1=470$ Da. Mp 178–181C. $^1$HNMR (400 MHz, DMSO-$d_6$) δ 11.65 (s, 1H), 11.53 (s, 1H), 9.32 (s, 1H), 7.71 (s, 1H), 7.65 (d, J=8.4 Hz, 1H), 7.51–7.47 (m, 1H), 733–729 (m, 1H), 7.16 (d, J=8.4 Hz, 1H), 6.75 (s, 1H), 4.20–4.18 (m, 2H), 3.81 (s, 3H), 3.55–3.53 (m, 2H), 3.40–3.37 (m, 2H), 1.06–1.02 (m, 3H).

Example 48

Carbamic Acid, [[[5[[(3,4-difluorophenyl)amino]carbonyl]-2-methoxyphenyl]amino]sulfonyl]-, 2-ethoxyethyl ester The title compound was synthesized as in Example 1 using 2-ethoxyethanol (0.40 mL, 4.0 mmol), CSI (0.42 mL, 4.9 mmol), and 3-amino-N-(3,4-difluoro-phenyl)-4methoxy-benzamide (1.0 g, 3.6 mmol) to give 0.95 g of carbamic acid, [[[5-[[(3,4-difluorophenyl)amino]carbonyl]-2-methoxyphenyl]-amino]sulfonyl]-, 2-ethoxyethyl ester. Microanalysis: $C_{19}H_{21}F_2N_3O_7S$; calculated: C=48.20; H=4.47; N=8.88. found. C=48.29; H=4.48; N=8.80. MS: $M^++1=474$ Da. Mp 179–182° C. $^1$HNMR (400 MHz, DMSO-$d_6$) δ 11.51 (s, 1H), 10.34 (s, 1H), 9.44 (s, 1H), 7.96–7.87 (m, 3H), 7.54–7.52 (m, 1H), 7.42 (q, J=10.1, 9.2 Hz, 1H), 720 (d, J=8.4 Hz, 1H), 4.18 (t, J=43 Hz, 2H), 3.85 (s, 3H), 3.54 (t, J=4.6 Hz, 2H), 3.41 (q, J=7.0 Hz, 2H), 1.06 (t, J=7.0 Hz, 3H).

Example 49

Carbamic Acid, [[[5-(5,6-difluoro-IH-indol-2-yl)-2-methoxyphenyl]-amino]sulfonyl]-3-(phenylmethoxy)propyl ester The title compound was synthesized as in Example 1 using 3-benzyloxy-1-propanol (0.65 mL, 4.0 mmol), CSI (0.42 mL, 4.9 mmol), and 5-(5,6-difluoro-1H-indol-2-yl)-2-methoxy-phenylamine (1.0 g, 3.6 mmol) to give 0.84 g of carbamic acid, [[[5-(5,6-difluoro-1H-indol-2-yl)$_2$-methoxyphenyl]amino]sulfonyl]-3-(phenylmethoxy)propyl ester. Microanalysis: $C_{26}H_{25}F_2N_3O_6S$; calculated: C=57.24; H=4.62; N=7.70; found: C=56.93; H=4.61; N=7.84. MS: $M^++1=546$ Da. Mp 166–168° C. $^1$HNMR (400 MHz, DMSO-$d_6$) δ 11.62 (s, 1H), 11.40 (s, 1H), 9.32 (s, 1H), 7.68 (s, 1H), 7.62 (d, J=8.7 Hz, 1H), 7.48–7.43 (m, 1H), 7.30–7.22 (m, 6H), 7.11 (d, J=8.4 Hz, 1H), 6.72 (s, 1H), 4.35 (s, 2H), 4.12 (t, J=6.3 Hz, 2H), 3.75 (s, 3H), 3.41 (t, J=6.0 Hz, 2H), 1.84–1.78 (m, 2H).

Example 50

Carbamic Acid, [[[5-[[(3,4-difluorophenyl)amino]carbonyl]-2-methoxyphenyl]amino]sulfonyl]-, 3-(phenylmethoxy)propyl ester The title compound was synthesized as in Example 1 using 3-benzyloxy-1-propanol (0.65 mL, 4.0 mmol), CSI (0.42 mL, 4.9 mmol), and 3-amino-N-(3,4-difluorophenyl)-4-methoxy-benzamide (1.0 g, 3.6 mmol) to give 1.11 g of carbamic acid, [[[5-[[(3,4-difluorophenyl)amino]carbonyl]-2-methoxyphenyl]amino]sulfonyl]-, 3-(phenylmethoxy)propyl ester. Microanalysis: $C_{25}H_{25}F_2N_3O_7S$; calculated: C=54.21; H=4.64; N=7.59. found: C=54.21; H=4.60; N=7.72. MS: $M^++1=550$ Da. Mp 178–179° C. $^1$HNMR (400 Mz, DMSO-$d_6$) δ 11.40 (s, 1H), 10.33 (s, 1H), 9.44 (s, 1H), 7.96–7.87 (m, 3H), 7.54 (m, 1H), 7.53 (q, J=2.2, 1.7 Hz, 1H), 7.43–7.25 (m, 6H), 7.19 (d, J=8.7 Hz, 1H), 4.43 (s, 2H), 4.16 (t, J=6.5 Hz, 2H), 3.83 (s, 3H), 3.47 (t, J=6.3 Hz, 2H), 1.06 (m, 2H).

Example 51

Carbamic Acid, [[[5-(5,6-difluoro-IH-indo-2yl)-methoxyphenyl]amino]-sulfonyl]-hexyl ester The title compound was synthesized as in Example 1 using hexanol (0.50 mL, 4.0 mmol), CSI (0.42 mL, 4.9 mmol), and 5-(5,6-difluoro-1H-indol-2-yl)-2-methoxy-phenylamine (1.0 g, 3.6 mmol) to give 0.79 g of carbamic acid, [[[5-(5,6-difluoro-IH-indol-2-yl)-2-methoxyphenyl]amino]sulfonyl]-hexyl ester. Microanalysis: $C_{22}H_{25}F_2N_3O_5S$; calculated: C=54.88; H=5.23; N=8.73; found: C=55.05; H=5.14; N=8.64. MS: $M^++1=482$ Da. Mp 186–188° C. $^1$HNMR (400 Mz, DMSO-$d_6$) δ 11.66 (s, 1H), 9.27 (s, 1H), 7.72 (s, 1H), 7.66 (d, J=6.8 Hz, 1H), 7.52–7.47 (m, 1H), 7.34–7.30 (m, 1H), 7.17 (d, J=8.7 Hz, 1H), 6.76 (s, 1H), 4.08–4.05 (m, 2H), 3.82 (s, 3H), 1.55–1.50 (m, 2H), 1.22 (s, 6H), 0.84–0.80 (m, 3H).

Example 52

Carbamic Acid, [[[5-[[(3,4-difluorophenyl)amino]carbonyl]-2methoxyphenyl]amino]sulfonyl]-, Hexyl ester The title compound was synthesized as in Example 1 using hexanol (0.50 mL, 4.0 mmol), CSI (0.42 mL, 4.9 mmol), and 3-amino-N-(3,4-difluoro-phenyl)-4-methoxy-benzamide (1.0 g, 3.6 mmol) to give 0.76 g of carbamic acid, [[[5-[[(3,4-difluorophenyl)amino]carbonyl]-2-methoxyphenyl]amino]sulfonyl]-, hexyl ester. Microanalysis: $C_{21}H_{25}F_2N_3O_6S$; calculated: C=51.95; H=5.19; N=8.65. found: C=51.90; H=5.09; N=8.40. MS: $M^++1$=486 Da. Mp 175–178° C. $^1$HNMR (400 MHz, DMSO-$d_6$) δ 11.36 (s, 1H), 10.31 (s, 1H), 9.33 (s, 1H), 7.96–7.88 (m, 3H), 7.56–7.54 (m, 1H), 7.42 (q, J=92, 8.9 Hz, 1H), 7.21 (d, J=8.7 Hz, 1H), 4.07 (t, J=6.5 Hz, 2H), 3.87 (s, 3H), 1.55–1.54 (m, 2H), 1.26 (s, 6H), 0.86–0.84 (m, 3H).

Example 53

Carbamic Acid, [[[5-(5,6-difluoro-indol-2-yl)-2-methoxyphenyl]amino]-sulfonyl]-, 1,1-dimethylethyl ester The title compound was synthesized as in Example 1 using t-butyl alcohol (2.0 mL, 20.9 mmol), CSI (2.0 mL, 23.0 mmol), and 5-(5,6-difluoro-1H-indol-2-yl)-2-methoxy-phenylamine (2.5 g, 9.1 mmol) to give 3.28 g of carbamic acid, [[[5-(5,6-difluoro-IH-indol-2-yl)-2-methoxyphenyl]amino]sulfonyl]-, 1,1-dimethylethyl ester. Microanalysis: $C_{20}H_{21}F_2N_3O_5S$·0.06 $C_6H_{16}NCl$·0.22 $H_2O$; calculated: C=52.97; H=4.85; N=9.20. found: C=52.51; H=4.85; N=9.20. MS: $M^++1$=454 Da. Mp 158–160° C. $^1$HNMR (400 MHz, DMSO-$d_6$) δ 11.64 (s, 1H), 11.17 (s, 1H), 8.99 (s, 1H), 7.71 (s, 1H), 7.61 (d, J=6.5 Hz, 1H), 7.51–7.46 (m, 1H), 7.32–7.28 (m, 1H), 7.15 (d, J=8.7 Hz, 1H), 6.72 (s, 1H), 3.82 (s, 3H), 1.36 (s, 9H).

Example 54

Sulfamide, [5-(5,6-difluoro-IH-indol-2-yl)-2-methoxyphenyl]

Carbamic acid, [[[5-(5,6-difluoro-IH-indol-2-yl)-2-methoxyphenyl]amino]sulfonyl]-1,1-dimethylethyl ester (2.0 g, 4.4 mmol) and anisole (1.5 mL, 13.8 mmol) were stirred in trifluoroacetic acid (20 mL) for 0.5 hour. The excess trifluoroacetic acid was evaporated under reduced pressure to give a white solid, which was triturated with ether and dried. Yield 1.14 g of sulfamide, [5-(5,6-difluoro-IH-indol-2-yl)-2-methoxyphenyl]-. Microanalysis: $C_{15}H_{13}F_2N_3O_3S$; calculated: C=50.99; H=3.71; N=11.89; found: C=50.90; H=3.83; N=11.50. MS: $M^++1$=354 Da. Mp 177–180° C.

Example 55

Benzamide, 3-[(aminosulfonyl)amino]-N-(3,4-difluorophenyl)-4-methoxy

Carbamic acid, [[[5-[[(3,4-difluorophenyl)amino]carbonyl]-2-methoxyphenyl]amino]sulfonyl]-, 1,1-dimethylethyl ester (0.28 g, 0.6 mmol) and anisole (0.33 mL, 3.1 mmol) were stirred in trifluoroacetic acid (10 mL) for 0.5 hour. The excess trifluoroacetic acid was evaporated under reduced pressure to give a white solid, which was triturated with ether and dried. Yield 0.16 g of benzamide, 3-[(aminosulfonyl)amino]-N-(3,4-difluorophenyl)-4methoxy-. Microanalysis: $C_{14}H_{13}F_2N_3O_4S$; calculated: C=46.04; H=3.52; N=11.36; found: C=46.02; H=3.60; N=11.36. MS: $M^{++}1$=358 Da. Mp 167–170° C.

Example 56

Carbamic Acid, [[[5-[[(3,4-difluorophenyl)amino]carbonyl]-2-methoxyphenyl]amino]sulfonyl]-, 2-(1,3-dihydro-1,3-dioxo-2H-isoindol-2-yl)ethyl ester The title compound was synthesized as in Example 1 using N-hydroxyethyl phthalimide (2.2 g, 11.5 mmol), CSI (1.0 mL, 11.5 mmol), and 3-amino-N-(3,4-difluorophenyl)-4-methoxy-benzamide (1.5 g, 5.4 mmol) to give 0.98 g of carbamic acid, [[[5-[[(3,4-difluorophenyl)amino]carbonyl]-2-methoxyphenyl]amino]sulfonyl]-, 2-(1,3-dihydro-1,3-dioxo-2H-isoindol-2-yl)-ethyl ester. Microanalysis: $C_{25}H_{20}F_2N_4O_8S$; calculated: C=51.68; H=3.59; N=9.64. found: C=51.69; H=3.38; N=9.61. MS: $M^++1$=575 Da. Mp 203–205° C. $^1$HNMR (400 MHz, DMSO-$d_6$) δ 11.42 (s, 1H), 10.30 (s, 1H), 9.38 (s, 1H), 7.93–7.80 (m, 7H), 7.52–7.50 (m, 1H), 7.39 (q, J=9.2, 10.6 Hz, 1H), 7.15 (d, J=8.7 Hz, 1H), 429 (t, J=5.8 Hz, 2H), 3.84 (t, J=5.8 Hz, 2H), 3.80(s, 3H).

Example 57

Benzamide, N-(3,4-difluorophenyl-3-[[[[(dimethylamino)sulfonyl]-amino]-carbonyl]amino]-4-methoxy 3-Amino-N-(3,4-difluoro-phenyl)-4-methoxy-benzamide (2.0 g, 7.2 mmol) was dissolved in 50 mL of methylene chloride and cooled to 0° C. Chlorosulfonyl isocyanate (0.85 mL, 9.8 mmol) dissolved in 20 mL of methylene chloride was added dropwise. The mixture was stirred overnight. The resulting solid was collected by filtration and dried under vacuum. The dried solid (1.0 g, 2.4 mmol) was sited in 50 mL of methylene chloride with triethylamine (0.7 mL, 4.8 mmol) for 1 hour. Dimethylamine (1.2 mL of a 2N solution, 2.4 mmol) was added, and the solution stirred for 48 hours. The resulting mixture was washed with water (2×50 mL) and the organic phase dried over magnesium sulfate. The solvents were evaporated under reduced pressure to give a foam. The foam was redissolved in a small amount of fresh methylene chloride and treated with 1N hydrochloric acid (20 mL). Vigorous shaking produced a precipitate, which was collected via filtration. The resulting powder was sequentially triturated with water, methylene chloride, and ether. The triturated solid was dried under vacuum to give 0.64 g of benzamide, N-(3,4-difluorophenyl)-3-[[[[(dimethylamino)sulfonyl]-amino]carbonyl]amino]-4-methoxy-. Microanalysis: $C_{17}H_{18}F_2N_4O_5S$·0.86 $H_2O$; calculated: C=46.00; H=4.31; N=12.69. found: C=46.00; H=4.31; N=12.69. MS:$M^++1$=349 Da. Mp 253–255° C. $^1$HNMR (400 MHz, DMSO-$d_6$) δ 10.34 (s, 1H), 10.25 (s, 1H), 9.26 (s, 1H), 7.94–7.89 (m, 1H), 7.85 (d, J=8.7 Hz, 1H), 7.64 (s, 1H), 7.49–7.39 (m, 2H), 7.27 (d, J=8.4 Hz, 1H), 3.92 (s, 3H), 2.95 (s, 6H).

Example 58

Carbamic acid, [[[5-[[(3,4-difluorophenyl)amino]carbonyl]-2-methoxyphenyl]amino]sulfonyl]-, 1,1-dimethylethyl ester The title compound was synthesized as in Example 1 using t-butyl alcohol (1.8 mL, 19.1 mmol), CSI (2.0 mL, 23.0 mmol), and 3-amino-N-(3,4-difluoro-phenyl)-4-methoxy-benzamide (5.3 g, 19.1 mmol) to give 0.84 g of carbamic acid, [[[5-[[(3,4-difluorophenyl)amino]carbonyl]-2-methoxyphenyl]amino]sulfonyl]-, 1,1-dimethylethyl ester. Microanalysis: $C_{19}H21F_2N_3O_6S$; calculated: C=49.89; H=4.63; N=9.19. found: C=49.81; H=4.48; N=9.14. MS: $M^++1$=456 Da. Mp 193–194° C.

Example 59

Benzamide, N-(3,4-difluorophenyl)-3-[[[[[4-(1,1-dimethylethyl)phenyl]-amino]carbonyl]amino] sulfonyl]amino]-4-methoxy The title compound was synthesized as in Example 1 using 4-t-butyl aniline (1.3 mL, 8.1 mmol), CSI (0.85 mL, 9.8 mmol), and 3-amino-N-(3,4-difluoro-phenyl)-4-methoxy-benzamide (1.9 g, 6.8 mmol) to give 0.095 g of benzamide, N-(3,4-difluorophenyl)-3-[[[[[4-(1,1-dimethylethyl)phenyl]amino]carbonyl]amino]sulfonyl] amino]-4-methoxy-. Microanalysis: $C_{25}H_{26}F_2N_4O_5S\cdot_{0.46}$ $H_2O$; calculated: C=55.52; H=5.02; N=10.36. found: C=55.46; H=4.94; N=10.40. MS: $M^++1$=533 Da. Mp 199–202° C.

Example 60

Benzamide, N-(3,4-difluorophenyl)-4-methoxy-3-[[[[[(3-nitrophenyl)-amino]carbonyl]amino] sulfonyl]amino]

The title compound was synthesized as in Example 1 using 3-nitroaniline (1.35 g, 9.8 mmol), CSI (0.85 L, 9.8 mmol), and 3-amino-N-(3,4-difluoro-phenyl)-4-methoxy-benzamide (0.39 g, 1.4 mmol) to give 0.074 g of benzamide, N-(3,4-difluorophenyl)-4-methoxy-3-[[[[[(3-nitrophenyl)-amino]carbonyl]-amino]sulfonyl]amino]-. Microanalysis: $C_{21}H_{17}F_2N_5O_7S.0.44$ $H_2O$; calculated: C=47.65; H=3.40; N=13.23. found: C=47.64; H=3.01; N=13.51. MS: $M^++1$= 522 Da.Mp 206–208° C.

Example 61

Benzamide, 3-[[[[[(3-chlorophenyl)amino]carbonyl] amino]sulfonyl]amino]-N-(3,4-difluorophenyl)-4-methoxy The title compound was synthesized as in Example 1 using 3-chloroaniline (2.0 mL, 18.9 mmol), CSI (2.0 mL, 23.0 mmol), and 3-amino-N-(3,4difluoro-phenyl)-4-methoxy-benzamide (1.39 g, 5.0 mmol) to give 0.030 g of benzamide, 3-[[[[[(3-chlorophenyl)amino]carbonyl]amino] sulfonyl]amino]-N-(3,4-difluorophenyl)-4-methoxy-. Microanalysis: $C_{21}H_{17}ClF_2N_4O_5S$; calculated: C=49.37; H=3.35; N=10.97. found: C=48.97; H=3.11; N=10.78. MS: $M^++1$=511 Da. Mp 193–196° C.

Example 62

Benzamide, 3-[[[[[[3,5-bis(trifluoromethyl)phenyl] amino]-carbonyl]amino]-sulfonyl]amino]-N-(3,4-difluorophenyl)-4-methoxy The title compound was synthesized as in Example 1 using 3,5-bis(trifluoromethyl)aniline (1.3 mL, 8.2 mmol), CSI (0.85 mL, 9.8 mmol), and 3-amino-N-(3,4-difluorophenyl)-4-methoxy-benzamide (0.63 g, 2.3 mmol) to give 0.032 g of benzamide, 3-[[[[[[3,5-bis (trifluoromethyl)phenyl]amino]-carbonyl]amino]sulfonyl] amino]-N-(3,4-difluorophenyl)-4-methoxy-. Microanalysis: $C_{23}H_{16}F_8N_4O_5S.1.63$ $H_2O$; calculated: C=43.04; H=3.02; N=8.73. found: C=43.05; H=2.68; N=8.55. MS: $M^+-1$=611 Da. Mp 175–178° C.

Example 63

Benzamide, 3-[[[[[(4-aminophenyl)amino]carbonyl] amino]sulfonyl]amino]-N-(3,4-difluorophenyl)-4-methoxy-, mono(trifluoroacetate)

Chlorosulfonyl isocyanate (1.0 mL, 12.0 mmol) was dissolved in 20 mL of methylene chloride and cooled to 0° C. BOC-1,4-Phenylenediamine (2.5 g, 12.0 mmol) dissolved in 20 mL of methylene chloride was added dropwise to the chlorosulfonyl isocyanate solution. Upon stirring, a precipitate slowly formed. After 2 hours, the mixture was filtered, and the solid collected and dried. Yield 2.92 g. A portion of this solid (0.92 g, 2.7 mmol) was placed in a flask containing 3-amino-N-(3,4-difluoro-phenyl)-4-methoxy-benzamide (0.75 g, 2.7 mmol), triethylamine (1.0 mL, 6.8 mmol) and 50 mL of tetrahydrofuran. The mixture was heated to 50° C., and sired overnight The tetrahydrofuran was removed under reduced pressure; the resulting solid was triturated with methanol and dried under vacuum. Yield 0.32 g. A portion of this solid (0.20 g, 0.3 mmol) was stirred with anisole (0.4 mL, 3.7 mmol) in trifluoroacetic acid (20 mL). After stirring for 1 hour, the trifluoroacetic acid was removed under reduced pressure. The resulting oil was triturated with ether, resulting in a solid. The solid was dried under vacuum; yield 0.20 g of benzamide, 3-[[[[[(4-aminophenyl)amino] carbonyl]-amino]sulfonyl]amino]-N-(3,4-difluorophenyl)-4-methoxy-, mono(trifluoroacetate). Microanalysis: $C_{21}H_{19}F_2N_5O_5S.0.69$ $C_2HO_2F_3.2.6$ $H_2O$; calculated: C=43.62; H=3.96; N=11.36. found: C=43.99; H=3.56; N=11.20. Mp 18& 189° C.

Example 64

Benzamide, N-(3,4-difluorophenyl)methoxy-3-[[[[[[3-(trifluoromethyl)phenyl]amino]carbonyl] amino]sulfonyl]amino]

The title compound was synthesized as in Example 1 using 3-trifluoromethylaniline (1.32 g, 10.6 mmol), CSI (0.85 mL, 9.8 mmol), and 3-amino-N-(3,4-difluoro-phenyl)-4-methoxy-benzamide (0.92 g, 3.3 mmol) to give 0.060 g of benzamide, N-(3,4-difluorophenyl)-4-methoxy-3-[[[[[3-(trifluoromethyl)phenyl]amino]carbonyl]amino]sulfonyl] amino]-. Microanalysis: $C_{22}H_{17}F_5N_4O_5S$; calculated: C=48.53; H=3.15; N=10.29. found: C=48.52; H=3.09; N=10.18. MS: $M^++1$=545 Da. Mp 198–200° C.

Example 65

Benzoic Acid, 4-[[[[[5-[[(3,4-difluorophenyl) amino]carbonyl]-2-methoxyphenyl]amino]sulfonyl] amino]carbonyl]amino]

Chlorosulfonyl isocyanate (1.7 mL, 19.5 mmol) was dissolved in 20 mL of methylene chloride and cooled to 0° C. Methyl 4-aminobenzoate (2.5 g, 16.2 mmol) dissolved in 20 mL of methylene chloride was added dropwise to the chlorosulfonyl isocyanate solution. Upon stirring, a precipitate slowly formed. After 2 hours, the mixture was filtered, and the solid collected and dried; yield 4.21 g. A portion of this solid (1.0 g, 3.4 mmol) was placed in a flask containing 3-amino-N-(3,4-difluoro-phenyl)-4-methoxy-benzamide (0.95 g, 3.4 mmol), triethylamine (1.2 mL, 8.5 mmol), and 50 mL of tetrahydrofuran. The mixture was stirred overnight. The tetrahydrofuran was evaporated under reduced pressure, and the resulting solid was dissolved in methylene chloride (50 mL). The methylene chloride was sequentially washed with 25 mL of 1N hydrochloric acid, water, and brine. A precipitate was formed, which was recovered by filtration and triturated with a mixture of methylene chloride and methanol. The solid was dried under vacuum; yield 0.67 g. A portion of this solid (0.30 g, 0.6 mmol) was suspended in a 9:1 mixture of tetrahydrofuran and water (10 mL). Lithium hydroxide (48.3 mg, 2.0 mmol) was added, and the resulting mixture was refluxed overnight. The mixture was diluted with 1N hydrochloric acid (50 mL) and extracted with diethyl ether (1×50 mL) and ethyl acetate (1×50 mL). The organics were combined, dried with magnesium sulfate, and filtered. The resulting filtrate was evaporated under reduced pressure to give a white foam. The foam was triturated with hot ethyl acetate and ether, then dried under vacuum to give 0.12 g of benzoic acid, 4-[[[[[5-[[(3,4-difluorophenyl)amino]carbonyl]-2-methoxyphenyl]amino]sulfonyl]amino]carbonyl]amino]-. Microanalysis for $C_{22}H_{18}F_2N_4O_7S \cdot 0.25\ H_2O \cdot 0.1\ C_4H_8O_2$; calculated C=50.40; H=3.64; N=10.50. found: C=50.29; H=3.71; N=10.14.

Example 66

Benzamide, N-(3,4-difluorophenyl)-4-methoxy-3-[[[[[(4-methoxyphenyl)-amino]carbonyl]amino]sulfonyl]amino]

The title compound was synthesized as in Example 1 using p-anisidine (1.0 g, 7.1 mmol), CSI (0.85 mL, 9.8 mmol), and 3-amino-N-(3,4-difluoro-phenyl)-4-methoxy-benzamide (1.75 g, 6.3 mmol) to give 0.43 g of benzamide, N-(3,4-difluorophenyl)-4-methoxy-3-[[[[[(4-methoxyphenyl)amino]-carbonyl]amino]sulfonyl]amino]-. Microanalysis: $C_{22}H_{20}F_2N_4O_6S$; calculated: C=52.17; H=3.98; N=11.06. found: C=52.17; H=3.89; N=10.95. Mp 189–192° C.

Example 67

Benzamide, N-(3,4-difluorophenyl)-4-methoxy-3-[[[[(phenylamino)carbonyl]-amino]sulfonyl]amino]

The title compound was synthesized as in Example 1 using p-toluidine (0.87 g, 8.1 mmol), CSI (0.85 mL, 9.8 mmol), and 3-amino-N-(3,4-difluoro-phenyl)-4-methoxy-benzamide (0.56 g, 2.0 mmol) to give 0.25 g of benzamide, N-(3,4-difluorophenyl)-4-methoxy-3-[[[[(phenylamino)carbonyl]amino]-sulfonyl]amino]-. Microanalysis: $C_{22}H_{20}F_2N_4O_5S$; calculated: C=53.87; H=4.11; N=11.42. found: C=53.56; H=4.14; N=11.27. MS: $M^++1=491$ Da. Mp 194–197° C.

Example 68

Benzamide, 3-[[[[[(4-chlorophenyl)amino]carbonyl]amino]sulfonyl]amino]-N-(3,4-difluorophenyl)-4-methoxy The title compound was synthesized as in Example 1 using 4-chloroaniline (1.0 g, 8.1 mmol), CSI (0.85 mL, 9.8 mmol), and 3-amino-N-(3,4-difluoro-phenyl)-4-methoxy-benzamide (1.17 g, 4.2 mmol) to give 0.24 g of benzamide, 3-[[[[[(4-chlorophenyl)amino]carbonyl]amino]sulfonyl]amino]-N-(3,4-difluorophenyl)-4-methoxy-. Microanalysis: $C_{21}H_{17}ClF_2N_4O_5S$; calculated: C=49.37; H=3.35; N=10.97. found: C=49.15; H=3.17; N=10.70. MS: $M^++1=511$ Da. Mp 195–198° C.

Example 69

Carbamic Acid, [[[5-[[(3,4-difluorophenyl)amino]carbonyl]-2-methoxyphenyl]amino]sulfonyl]methyl-, Ethyl ester The title compound was synthesized as in Example 13 using carbamic acid, [[[5-[[(3,4-difluorophenyl)amino]carbonyl]-2-methoxyphenyl]amino]-sulfonyl]-, ethyl ester (1.0 g, 2.3 mmol), DBU (0.43 g, 1.2 eq, 2.8 mmol), and methyl iodide (0.29 mL, 2 eq, 4.7 mmol) to give carbamic acid, [[[5-[[(3,4-difluorophenyl)amino]carbonyl]-2-methoxyphenyl]amino]sulfonyl]methyl-, ethyl ester as a white solid. Microanalysis: $C_{18}H_{19}F_2N_3O_6S_1$; calculated: C=48.76; H=4.32; N=9.48. found: C=48.76; H=4.25; N=9.30. MS: $M^++1=444$ Da.

Examples of assays useful for characterizing the biological effects of the compounds of the present invention on the 15-LO cascade are described below.

Biological Example 1
Rabbit Reticulocyte 15-LO Assay (H15LO)

The H15LO assay measures inhibition of 15-LO catalyzed oxidation of linoleic acid to the hydroperoxy fatty acid 13-(S)HPODE, a conjugated diene. In the H15LO assay, a test compound was incubated with 15-LO enzyme in the presence of the linoleic acid substrate. For example, 2 units (U) of rabbit reticulocyte 15-LO and 174 $\mu$M linoleic acid were incubated with a known amount of a test compound of the present invention for 15 minutes at 4° C. The total reaction volume was 100 $\mu$L in phosphate buffer saline (PBS) containing 0.2% sodium cholate. The reaction was stopped with 100 $\mu$L of mobile phase and 10 mL of triethyl phosphite. The resulting 13-(S)HPODE was essentially quantitatively reduced with triethyl phosphite to the more stable 13-hydroxyoctadecadienoate (13-HODE), which prevents artificial, nonenzymatic lipidperoxidation and product breakdown in the sample. 13-HODE was quantitated by comparing peak areas of individual samples with those from a standard curve generated using authentic 13-HODE. The test reaction was compared to a control reaction, which was identical to the test reaction except no test compound of the present invention was present Percent inhibition was calculated as the amount of 13-HODE produced by the test reaction divided by the amount of 13-HODE produced by the control reaction, expressed as a percent The results for certain compounds of the present invention are reported below in Table 1 in the column headed "H15LO $IC_{50}$ (nM)" as an $IC_{50}$ in nM or the concentration of compound of the present invention in nanomolar required to inhibit 15-LO catalyzed oxidation by 50%.

15-LO is obtained from phenylhydrazine-treated rabbits and purified according to the method of Rapoport (Rapoport et al., *European Journal of Biochemistry*, 1979;96:545–561).

Biological Example 2
Monocyte Recruitment

The recruitment or chemotaxis of monocytes is assayed by methods well known to those skilled in the art. In particular, the method set forth in *J. Clin. Invest.*, 1988;82:1853–1863, which is hereby incorporated by reference, can be used.

Biological Example 3
Human Lysate 15-LO Assay (HUM15LO)

The HUM15LO assay measures inhibition of 15-LO catalyzed oxidation of linoleic acid to the hydroperoxy fatty acid 13-(S)HPODE, a conjugated diene. In the HUM15LO assay, a test compound of the present invention was incubated with 15-LO enzyme in the presence of the linoleic acid substrate. For example, a known amount of a test compound of the present invention, 100 µL of human 15-LO, and 174 µM linoleic acid in PBS containing 0.2% sodium cholate were incubated for 15 minutes at 4° C. The reaction was stopped with 100 µL of mobile phase and 10 µL of triethyl phosphite. 13-(S)HPODE was essentially quantitatively reduced with triethyl phosphite to the more stable 13-hydroxyoctadecadienoate (13-HODE), which prevents artificial, nonenzymatic lipidperoxidation and product breakdown in the sample. 13-HODE was quantitated by comparing peak areas of individual samples with those from a standard curve generated using authentic 13-HODE. The test reaction is compared to a control reaction, which is identical to the test reaction except no test compound of the present invention is present Percent inhibition is calculated as the amount of 13-HODE produced by the test reaction divided by the amount of 13-HODE produced by the control reaction, expressed as a percent. The results for certain compounds of the present invention are reported below in Table 1 in the column headed "HUM15LO $IC_{50}$ (nM)" as an $IC_{50}$ in nM or the concentration of compound of the present invention in nanomolar required to inhibit 15-LO catalyzed oxidation by 50%.

Human 15-LO was generated in a recombinant 15-lipoxygenase bacculovirus expression system, using Gibco/BRL/Life Technologies' Bac-to-Bac expression reagents; T4 DNA ligase, Kanamycin, Gentamicin, tetracycline, penicillin, streptomycin, Bluo-gal, IPTG, DH10Bac competent cells, SOC, LB medium, Sf-900 II SFM media, Sf9 insect cells, Cell Fectin, and EcoRI, BamHI and KpnI restriction enzymes.

TABLE 1

| Ex. | HUM15LO $IC_{50}$ (nM) | H15LO $IC_{50}$ (nM) |
|---|---|---|
| 20 | 1050 | N/A |
| 17 | 37 | 10 |
| 18 | 142 | N/A |
| 19 | 339 | N/A |
| 24 | 33 | 11 |
| 25 | 34 | 15 |
| 26 | 630 | N/A |
| 68 | 359 | N/A |
| 67 | 182 | N/A |
| 66 | 225 | 51 |
| 65 | 273 | 30 |
| 64 | 24 | N/A |
| 29 | 85 | 47 |
| 23 | 255 | N/A |
| 22 | 25 | 25 |
| 21 | 14 | 9 |
| 63 | 214 | N/A |
| 62 | 173 | N/A |
| 61 | 39 | 13 |
| 60 | 25 | N/A |
| 59 | 24 | 13 |
| 58 | 751 | N/A |
| 57 | N/A | N/A |
| 56 | 341 | N/A |
| 55 | 29 | 19 |
| 54 | 12 | 10 |
| 53 | N/A | 23 |
| 2 | 384 | N/A |
| 3 | 408 | N/A |
| 4 | 144 | N/A |
| 52 | 39 | 5 |
| 51 | 12 | 2 |
| 50 | 65 | 18 |
| 49 | 15 | 5 |
| 48 | 306 | N/A |
| 47 | 54 | 44 |
| 5 | 240 | N/A |
| 69 | 154 | N/A |
| 46 | 830 | N/A |
| 45 | 133 | 80 |
| 44 | 236 | N/A |
| 43 | 30 | 17 |
| 42 | 76 | 19 |
| 41 | 69 | 13 |
| 6 | N/A | N/A |
| 40 | 15 | 7 |
| 7 | 79 | N/A |
| 8 | 312 | N/A |
| 9 | 154 | N/A |
| 39 | N/A | N/A |
| 37 | 7 | 5 |
| 38 | 13 | 13 |
| 36 | 13 | 12 |
| 10 | N/A | N/A |
| 11 | N/A | N/A |
| 35 | N/A | N/A |
| 34 | 30 | 26 |
| 33 | N/A | N/A |
| 32 | 16 | 6 |
| 27 | 44 | 23 |
| 28 | 18 | 39 |
| 12 | N/A | N/A |
| 1 | 6 | 17 |
| 13 | 30 | 12 |
| 14 | N/A | N/A |
| 15 | N/A | N/A |
| 33 | 13 | 7 |
| 30 | 14 | 5 |
| 16 | 10 | 2 |

N/A = datum not available.

E. Uses

The disclosed compounds of Formula I will be formulated by standard methods into pharmaceutical compositions that are useful as prophylactic or therapeutic treatments for diseases modulated by the 15-LO cascade. The compositions will be administered to mammals for treating diseases with an inflammatory component, including inflammation and atherosclerosis.

1. Dosages

Those skilled in the art will be able to determine, according to known methods, the appropriate dosage for a patient, taking into account factors such as age, weight, general health, the type of pain requiring treatment, and the presence of other medications. In general, an effective amount will be between 0.1 and 1000 mg/kg per day, preferably between 1 and 400 mg/kg body weight, and daily dosages will be between 10 and 5000 mg for an adult subject of normal weight The dosages, however, may be varied depending upon the requirements of the patient, the severity of the condition being treated, and the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and ( ) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

Example 70

Tablet Formulation:

| Ingredient | Amount (mg) |
| --- | --- |
| The compound of Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administering to a human from one to four times a day for treatment of diseases responsive to the inhibition of the enzyme 15-lipoxygenase.

Example 71

Coated Tablets:

The tablets of Example 70 are coated in a customary manner with a coating of sucrose, potato starch, talc, tragacanth, and colorant.

Example 72

Injection Vials:

The pH of a solution of 500 g of the compound of Example 4 and 5 g of disodium hydrogen phosphate is adjusted to pH 6.5 in 3 L of doubled-distilled water using 2 M hydrochloric acid. The solution is sterile filtered, and the filtrate is filled into injection vials, lyophilized under sterile conditions, and aseptically sealed. Each injection vial contains 25 mg of the compound of Example 4.

Example 73

Suppositories:

A mixture of 25 g of the compound of Example 6, 100 g of soya lecithin, and 1400 g of cocoa butter is fused, poured into molds, and allowed to cool. Each suppository contains 25 mg of the compound of Example 6.

Example 74

Solution:

A solution is prepared from 1 g of the compound of Example 55, 9.38 g of $NaH_2PO_4.12H_2O$, 28.48 g of $Na_2HPO_4.12H_2O$, and 0.1 g benzalkonium chloride in 940 mL of double distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Example 55.

Example 75

Ointment:

500 mg of the compound of Example 21 is mixed with 99.5 g of petroleum jelly under aseptic conditions. A 5 g portion of the ointment contains 25 mg of the compound of Example 21.

Example 76

Capsules:

Two kilograms of the compound of Example 33 are filled into hard gelatin capsules in a customary manner such that each capsule contains 25 mg of the invention compound.

Example 77

Ampoules:

A solution of 2.5 kg of the compound of Example 60 is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Example 60.

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or the formation of an ester, pharmaceutical salt, hydrate, acid, or amide of a disclosed compound. Publications cited herein are hereby incorporated by reference in their entirety.

Having described the present invention above, various embodiments of the invention are hereupon claimed.

What is claimed is:

1. A compound of Formula I:

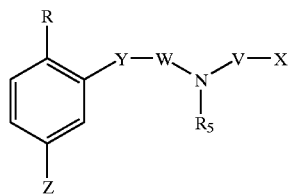

wherein:
R is OH, O—$C_{1-4}$ alkyl, or halo;
X is $R_1$, $OR_1$, $SR_1$, $NHR_1$, or $NR_1R_2$, wherein
$R_1$ and $R_2$ are independently selected from $C_1$–$C_{12}$ alkyl, $C_2$–$C_{12}$ alkenyl, $C_2$–$C_{12}$ alkynyl, benzyl, $C_3$–$C_7$ cycloalkyl, and phenyl,
wherein:
the alkyl, alkenyl, alkynyl, benzyl, and phenyl groups are optionally substituted with from 1 to 5 substituents independently selected from halo, $NHR_3$, $CF_3$, $C_1$–$C_6$ alkyl, $OR_4$, $CO_2R_3$, $NO_2$, and $SR_3$,
wherein $R_3$ and $R_4$ are independently H or $C_1$–$C_6$ alkyl;
W and V are independently $SO_2$ or C=O;
$R_5$ is H, $C_1$–$C_6$ alkyl, or benzyl, wherein benzyl is optionally substituted with $R_1$, wherein $R_1$ is as defined above, or $R_5$ is a pharmaceutically acceptable cation;
Y is $NR_6$ or O, wherein $R_6$ is H or $C_1$–$C_6$ alkyl;
Z is 2-indolyl, or 3-indolyl, which are optionally substituted with from 1 to 4 substituents independently selected from $C_1$–$C_6$ alkyl, fluoro, chloro, bromo, iodo, nitro, $NHR_7$, $NR_7R_8$, and $OR_7$,
wherein $R_7$ and $R_8$ are independently H or $C_1$–$C_6$ alkyl;
wherein:
each hydrocarbyl above is optionally substituted with from 1 to 3 substituents independently selected from halo, $C_1$–$C_6$ alkyl, $C_3$–$C_6$ cycloalkyl, $C_1$–$C_6$ alkenyl, $C_1$–$C_6$ alkynyl, phenyl, hydroxyl, amino, (amino)sulfonyl, N-acetyl, O-acetyl, $C_1$–$C_6$ thioalkyl, $C_1$–$C_6$ alkoxy, COOH, COO($C_1$–$C_6$ allyl), $SO_3Na$, $SO_3H$, $SO_2NH_2$, cyano, $CH_2NH_2$, acetyl, di($C_1$–$C_6$ alkyl)amino, and nitro, wherein the alkyl, cycloalkyl, alkenyl alkynyl, and phenyl substituents may be optionally substituted with from 1 to 3 substituents independently selected from halo, $C_1$–$C_6$ alkyl, hydroxyl, amino, and nitro; and pharmaceutically acceptable salts thereof.

2. A compound of claim 1, and pharmaceutically acceptable salts thereof, wherein Z is 2-indolyl, or 3-indolyl, which are optionally substituted with from 1 to 4 substituents independently selected from fluoro, chloro, and methyl.

3. A compound of claim 2, and pharmaceutically acceptable salts thereof, wherein Z is 2-indolyl, or 3-indolyl, which are substituted with from 1 to 3 substituents independently selected from halo, $C_1$–$C_6$ alkyl, $C_3$–$C_6$ cycloalkyl, $C_1$–$C_6$ alkenyl, $C_1$–$C_6$ alkyl, phenyl, hydroxyl, amino, (amino)sulfonyl, N-acetyl, O-acetyl, $C_1$–$C_6$ thioalkyl, $C_1$–$C_6$ alkoxy, COOH, COO($C_1$–$C_6$ allyl), $SO_3Na$, $SO_3H$, $SO_2NH_2$, cyano, $CH_2NH_2$, acetyl, di($C_1$–$C_6$ alkyl)amino, and nitro, wherein the alkyl, cycloalkyl, alkenyl, alkynyl, and phenyl substituents may be optionally substituted with from 1 to 3 substituents independently selected from halo, $C_1$–$C_6$ alkyl, $C_3$–$C_6$ cycloalkyl, $C_1$–$C_6$ alkenyl, $C_1$–$C_6$ alkynyl, phenyl, hydroxyl, amino, (amino)sulfonyl, N-acetyl, O-acetyl, $C_1$–$C_6$ thioalkyl, $C_1$–$C_6$ alkoxy, COOH, COO($C_1$–$C_6$ allyl), $SO_3Na$, $SO_3H$, $SO_2NH_2$, cyano, $CH_2NH_2$, acetyl, di($C_1$–$C_6$ alkyl)amino, and nitro, wherein the alkyl, cycloalkyl, alkenyl, alkynyl, and phenyl substituents may be optionally substituted with from 1 to 3 substituents independently selected from halo, $C_1$–$C_6$ alkyl, hydroxyl, amino, and nitro.

4. A compound of claim 1, and pharmaceutically acceptable salts thereof, wherein Z is 2-indolyl, or 3-indolyl, which are substituted with from 1 to 3 substituents selected from fluoro, chloro, bromo, and iodo.

5. A compound of claim 1, and pharmaceutically acceptable salts thereof, wherein Z comprises 2-indolyl optionally substituted with from 1 to 4 substituents independently selected from fluoro, chloro, and methyl.

6. A compound of claim 5, and pharmaceutically acceptable salts thereof, wherein Z is 5,6-difluoro-indol-2-yl.

7. A compound of claim 1, and pharmaceutically acceptable salts thereof, wherein $R_5$ is H.

8. A compound of claim 1, and pharmaceutically acceptable salts thereof, wherein $R_5$ is a cation selected from an alkali earth metal cation, an alkaline earth metal cation, ammonium, and choline.

9. A compound of claim 1, and pharmaceutically acceptable salts thereof, wherein $R_5$ is sodium cation, potassium cation, choline, or hemi calcium cation.

10. A compound of claim 1, and pharmaceutically acceptable salts thereof, wherein W is $SO_2$.

11. A compound of claim 1, and pharmaceutically acceptable salts thereof, wherein X is $R_1$, $OR_1$, $SR_1$, $NHR_1$, or $NR_1R_2$, wherein $R_1$ and $R_2$ are independently selected from $C_1$–$C_8$ alkyl, $C_2$–$C_8$ alkenyl, $C_2$–$C_8$ alkynyl, benzyl, $C_3$–$C_6$ cycloalkyl, and phenyl, wherein the alkyl, alkenyl, alkynyl, benzyl and phenyl groups are optionally substituted with from 1 to 3 substituents independently selected from halo, $C_1$–$C_6$ alkyl, $C_3$–$C_6$ cycloalkyl, $C_1$–$C_6$ alkenyl, $C_1$–$C_6$ alkynyl, phenyl, hydroxyl, amino, (amino)sulfonyl, N-acetyl, O-acetyl, $C_1$–$C_6$ thioalkyl, $C_1$–$C_6$ alkoxy, COOH, COO($C_1$–$C_6$ allyl), $SO_3Na$, $SO_3H$, $SO_2NH_2$, cyano, $CH_2NH_2$, acetyl, di($C_1$–$C_6$ alkyl)amino, and nitro, wherein the alkyl, cycloalkyl, alkenyl, alkynyl, and phenyl substituents may be optionally substituted with from 1 to 3 substituents independently selected from halo, $C_1$–$C_6$ alkyl, hydroxyl, amino, and nitro.

12. A compound of claim 1, and pharmaceutically acceptable salts thereof, wherein X is $R_1$, $OR_1$, $NHR_1$, or $NR_1R_2$, wherein $R_1$ and $R_2$ are independently selected from $C_2$–$C_5$ alkyl, $C_2$–$C_5$ alkenyl, $C_2$–$C_5$ alkynyl, benzyl, and phenyl, wherein the alkyl, alkenyl, alkynyl, benzyl, and phenyl groups are optionally substituted with from 1 to 3 substituents independently selected from halo, $C_1$–$C_6$ alkyl, $C_3$–$C_6$ cycloalkyl, $C_1$–$C_6$ alkenyl, $C_1$–$C_6$ alkynyl, phenyl, hydroxyl, amino, (amino)sulfonyl, N-acetyl, O-acetyl, $C_1$–$C_6$ thioalkyl, $C_1$–$C_6$ alkoxy, COOH, COO($C_1$–$C_6$ allyl), $SO_3Na$, $SO_3H$, $SO_2NH_2$, cyano, $CH_2NH_2$, acetyl, di($C_1$–$C_6$ alkyl)amino, and nitro, wherein the alkyl, cycloalkyl, alkenyl, alkynyl, and phenyl substituents may be optionally substituted with from 1 to 3 substituents independently selected from halo, $C_1$–$C_6$ alkyl, hydroxyl, amino, and nitro.

13. A compound of claim 1, wherein X is a phenylamino, phenoxy, alkoxy, alkylamino, dialkylamino, or (carboxy)alkoxy.

14. A compound according to claim 1 of Formula II

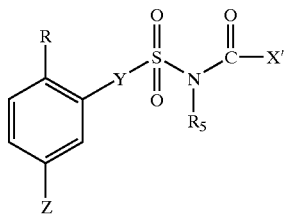

and pharmaceutically acceptable salts thereof, wherein X' is $OR_1$, $SR_1$, $NHR_1$, or $NR_1R_2$, wherein $R_1$ and $R_2$ are independently selected from $C_1$–$C_{12}$ alkyl, $C_2$–$C_{12}$ alkenyl, $C_2$–$C_{12}$ alkynyl, benzyl, $C_3$–$C_7$ cycloalkyl, and phenyl, wherein:
the alkyl, alkenyl, alkynyl, benzyl, and phenyl groups are optionally substituted with from 1 to 5 substituents independently selected from halo, $NHR_3$, $CF_3$, $C_1$–$C_6$ alkyl, $OR_4$, $CO_2R_3$, $NO_2$, and $SR_3$, wherein $R_3$ and $R_4$ are independently H or $C_1$–$C_6$ alkyl;

R is OH, O—$C_1$–$C_4$ alkyl, or halo;

Y is $NR_6$ or O, wherein $R_6$ is H or $C_1$–$C_6$ alkyl;

Z is 2-indolyl, or 3-indolyl, 2-benzimidazolyl, 2-benzoxazolyl, C(O)N(O)Ph, or N(O)C(O)Ph, which are optionally substituted with from 1 to 4 substituents independently selected from $C_1$–$C_6$ alkyl, fluoro, chloro, bromo, iodo, nitro, $NHR_7$, $NR_7R_8$, and $OR_7$, wherein $R_7$ and $R_8$ are independently H or $C_1$–$C_6$ alkyl; and $R_5$ is H, $C_1$–$C_6$ alkyl, or benzyl, optionally substituted with $R_1$, wherein $R_1$ is as defined above, or is a pharmaceutically acceptable cation.

15. A compound selected from the group consisting of:
Carbamic acid, [[[5-(5,6-difluoro-1H-indol-2-yl)-2-methoxyphenyl]amino]sulfonyl]-, dodecyl ester;
Carbamic acid, [[[5-(5,6-difluoro-1H-indol-2-yl)-2-methoxyphenyl]amino]sulfonyl]-, octyl ester;
Carbamic acid, [[[5-(5,6-difluoro-1H-indol-2-yl)-2-methoxyphenyl]amino]sulfonyl]-2-(dimethylamino)ethyl ester, monohydrochloride;
Acetic acid, [[[[[5-(5,6-difluoro-1H-indol-2-yl)-2-methoxyphenyl]amino]sulfonyl]-amino]carbonyl]oxy]-, phenylmethyl ester;
Carbamic acid, [[[5-(5,6-difluoro-1H-indol-2-yl)-2-methoxyphenyl]amino]sulfonyl]-, butyl ester;
Carbamic acid, [[[5-(5,6-difluoro-1H-indol-2-yl)-2-methoxyphenyl]amino]sulfonyl]-, 2-methylpropyl ester;
Urea, N-(3,5-dichlorophenyl)-]-N'-[[[5-(5,6-difluoro-1H-indol-2-yl)-2-methoxyphenyl]-amino]sulfonyl]-;
Carbamic acid, [[[5-(5,6-difluoro-1H-indol-2-yl)-2-methoxyphenyl]amino]sulfonyl]-, ethyl ester;
Carbamic acid, [[[5-(1H-indol-2-yl)-2-methoxyphenyl]amino]sulfonyl]-, ethyl ester;
Urea, N-(4-chlorophenyl)-N'-[[[5-(5,6-difluoro-1H-indol-2-yl)-2-methoxyphenyl]-amino]sulfonyl]-;
Urea, N-[[[5-(5,6-difluoro-1H-indol-2-yl)-2-methoxyphenyl]-amino]sulfonyl]-N'-(4-methylphenyl)-;
Carbamic acid, [[[5-(5,6-difluoro-1H-indol-2-yl)2-methoxyphenyl]amino]sulfonyl]-methyl ester;
Carbamic acid, [[[5-(5,6-difluoro-1H-indol-2-yl)-2-methoxyphenyl]amino]sulfonyl]-heptyl ester;
Carbamic acid, [[[5-(5,6-difluoro-1H-indol-2-yl)-2-methoxyphenyl]amino]sulfonyl]-pentyl ester;
Carbamic acid, [[[5-(5,6-difluoro-1H-indol-2-yl)-2-methoxyphenyl]amino]sulfonyl]-(2E)-3-phenyl-2-propenyl ester;
Carbamic acid, [[[5-(5,6-difluoro-1H-indol-2-yl)-2-methoxyphenyl]amino]sulfonyl]-2-(1-methylethoxy)ethyl ester;
Carbamic acid, [[[5-(5,6-difluoro-1H-indol-2-yl)-2-methoxyphenyl]amino]sulfonyl]-, phenylmethyl ester;
Carbamic acid, [[[5-(5,6-difluoro-1H-indol-2-yl)-2-methoxyphenyl]amino]sulfonyl]-2-phenylethyl ester;
Acetic acid, [[[[[5-(5,6-difluoro-1H-indol-2-yl)-2-methoxyphenyl]-amino]sulfonyl]amino]carbonyl]oxy]-, methyl ester;
Carbamic acid, [[[5-(5,6-difluoro-1H-indol-2-yl)-2-methoxyphenyl]amino]sulfonyl]-3-hydroxypropyl ester;
Carbamic acid, [[[5-(5,6-difluoro-1H-indol-2-yl)-2-methoxyphenyl]amino]sulfonyl]-, 2-ethoxyethyl ester;
Carbamic acid, [[[5-(5,6-difluoro-1H-indol-2-yl)-2-methoxyphenyl]amino]sulfonyl]-3(phenylmethoxy)propyl ester;
Carbamic acid, [[[5-(5,6-difluoro-1H-indol-2-yl)-2-methoxyphenyl]amino]sulfonyl]-hexyl ester; and
Carbamic acid, [[[5-(5,6-difluoro-1H-indol-2-yl)-2-methoxyphenyl]amino]sulfonyl]-, 1,1-dimethylethyl ester.

16. A pharmaceutical composition, comprising a therapeutically effective amount of a compound according to claim 1, or a pharmaceutically acceptable salt thereof, in admixture with a pharmaceutically acceptable carrier, diluent, or excipient.

* * * * *